United States Patent
Mescher

(10) Patent No.: US 10,595,831 B2
(45) Date of Patent: Mar. 24, 2020

(54) CONTROL FOR BIOPSY DEVICE

(71) Applicant: Devicor Medical Products, Inc., Cincinnati, OH (US)

(72) Inventor: Patrick A. Mescher, Bellbrook, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 908 days.

(21) Appl. No.: 14/991,419

(22) Filed: Jan. 8, 2016

(65) Prior Publication Data

US 2016/0120519 A1 May 5, 2016

Related U.S. Application Data

(62) Division of application No. 13/483,235, filed on May 30, 2012, now abandoned.

(51) Int. Cl.
*A61B 10/02* (2006.01)
*A61B 10/00* (2006.01)

(52) U.S. Cl.
CPC ...... *A61B 10/0275* (2013.01); *A61B 10/0096* (2013.01); *A61B 10/0283* (2013.01); *A61B 2010/0208* (2013.01); *A61B 2010/0225* (2013.01)

(58) Field of Classification Search
None
See application file for complete search history.

(56) References Cited

U.S. PATENT DOCUMENTS

| | | | |
|---|---|---|---|
| 3,630,192 A | 12/1971 | Jamshidi |
| 3,732,858 A | 5/1973 | Banko |
| 3,734,099 A | 5/1973 | Bender et al. |
| 3,889,657 A | 6/1975 | Baumgarten |
| 3,945,375 A | 3/1976 | Banko |
| 3,996,935 A | 12/1976 | Banko |
| 4,051,852 A | 10/1977 | Villari |
| 4,083,706 A | 4/1978 | Wiley |
| 4,203,444 A | 5/1980 | Bonnell et al. |

(Continued)

FOREIGN PATENT DOCUMENTS

| CN | 2397080 Y | 9/2000 |
|---|---|---|
| CN | 1722986 A | 1/2006 |

(Continued)

OTHER PUBLICATIONS

Chinese Office Action dated Mar. 17, 2017 for Application No. CN 2013800276960, 2 pages.

(Continued)

*Primary Examiner* — Matthew Kremer
(74) *Attorney, Agent, or Firm* — Frost Brown Todd LLC

(57) ABSTRACT

An exemplary biopsy system includes a biopsy device having a probe. The probe includes a distally extending needle and a cutter movable relative to the needle. The probe also includes a tissue sample holder detachably coupled to the proximal end of the probe. The biopsy system has a cycle where the biopsy system provides vacuum to the biopsy device, retracts the cutter to a proximal position, advances the cutter to a distal position, and transports a sample to the tissue sample holder. The biopsy system is capable of adjusting the duration of its cycle during operation of the biopsy device.

5 Claims, 15 Drawing Sheets

(56) References Cited

U.S. PATENT DOCUMENTS

| | | |
|---|---|---|
| 4,257,425 A | 3/1981 | Ryan |
| 4,316,465 A | 2/1982 | Dotson, Jr. |
| 4,320,761 A | 3/1982 | Haddad |
| 4,368,734 A | 1/1983 | Banko |
| 4,393,879 A | 7/1983 | Milgrom |
| 4,454,931 A | 6/1984 | Leiner et al. |
| 4,517,977 A | 5/1985 | Frost |
| 4,554,473 A | 11/1985 | Muller |
| 4,600,014 A | 7/1986 | Beraha |
| 4,767,601 A | 8/1988 | Kuerzinger et al. |
| 4,782,833 A | 11/1988 | Einhorn et al. |
| 4,783,317 A | 11/1988 | Kuerzinger et al. |
| 4,919,146 A | 4/1990 | Rhinehart et al. |
| RE33,258 E | 7/1990 | Onik et al. |
| 4,940,061 A | 7/1990 | Terwilliger et al. |
| 4,989,614 A | 2/1991 | Dejter, Jr. et al. |
| 4,995,877 A | 2/1991 | Ams et al. |
| 5,047,008 A | 9/1991 | de Juan, Jr. et al. |
| 5,074,756 A | 12/1991 | Davis |
| 5,108,381 A | 4/1992 | Kolozsi |
| 5,112,299 A | 5/1992 | Pascaloff |
| 5,133,359 A | 7/1992 | Kedem |
| 5,167,927 A | 12/1992 | Karlson |
| 5,188,118 A | 2/1993 | Terwilliger |
| 5,197,484 A | 3/1993 | Kornberg et al. |
| 5,213,110 A | 5/1993 | Kedem et al. |
| 5,217,478 A | 6/1993 | Rexroth |
| 5,217,479 A | 6/1993 | Shuler |
| 5,226,909 A | 7/1993 | Evans et al. |
| 5,228,055 A | 7/1993 | Uchida et al. |
| 5,231,110 A | 7/1993 | Seele et al. |
| 5,234,000 A | 8/1993 | Hakky et al. |
| 5,249,121 A | 9/1993 | Baum et al. |
| 5,249,583 A | 10/1993 | Mallaby |
| 5,275,609 A | 1/1994 | Pingleton et al. |
| 5,290,303 A | 3/1994 | Pingleton et al. |
| 5,295,980 A | 3/1994 | Ersek |
| 5,312,425 A | 5/1994 | Evans et al. |
| 5,320,110 A | 6/1994 | Wang |
| 5,320,635 A | 6/1994 | Smith |
| 5,341,816 A | 8/1994 | Allen |
| 5,353,804 A | 10/1994 | Kornberg et al. |
| 5,403,276 A | 4/1995 | Schechter et al. |
| 5,415,169 A | 5/1995 | Siczek et al. |
| 5,423,844 A | 6/1995 | Miller |
| 5,424,625 A | 6/1995 | Haner |
| 5,431,645 A | 7/1995 | Smith et al. |
| 5,432,065 A | 7/1995 | Fuller |
| 5,455,766 A | 10/1995 | Scheller et al. |
| 5,505,210 A | 4/1996 | Clement |
| 5,520,635 A | 5/1996 | Gelbfish |
| 5,526,822 A | 6/1996 | Burbank et al. |
| 5,543,695 A | 8/1996 | Culp et al. |
| 5,580,347 A | 12/1996 | Reimels |
| 5,601,585 A | 2/1997 | Banik et al. |
| 5,628,446 A | 5/1997 | Geiste et al. |
| 5,643,304 A | 7/1997 | Schechter et al. |
| 5,645,209 A | 7/1997 | Green et al. |
| 5,649,547 A | 7/1997 | Ritchart et al. |
| 5,669,923 A | 9/1997 | Gordon |
| 5,685,840 A | 11/1997 | Schechter et al. |
| 5,689,159 A | 11/1997 | Culp et al. |
| 5,769,086 A | 6/1998 | Ritchart et al. |
| 5,775,333 A | 7/1998 | Burbank et al. |
| 5,780,715 A | 7/1998 | Imblum |
| 5,791,908 A | 8/1998 | Gillio |
| 5,804,936 A | 9/1998 | Brodsky et al. |
| 5,823,998 A | 10/1998 | Yamagata |
| 5,848,978 A | 12/1998 | Cecchi |
| 5,871,454 A | 2/1999 | Majlessi |
| 5,876,329 A | 3/1999 | Harhen |
| 5,910,139 A | 6/1999 | Cochran et al. |
| 5,913,857 A | 6/1999 | Ritchart et al. |
| 5,928,164 A | 7/1999 | Burbank et al. |
| 5,944,673 A | 8/1999 | Gregoire et al. |
| 5,964,716 A | 10/1999 | Gregoire et al. |
| 5,976,164 A | 11/1999 | Bencini et al. |
| 5,980,469 A | 11/1999 | Burbank et al. |
| 6,007,497 A | 12/1999 | Huitema |
| 6,010,476 A | 1/2000 | Saadat |
| 6,013,956 A | 1/2000 | Anderson, Jr. |
| 6,017,316 A | 1/2000 | Ritchart et al. |
| 6,019,733 A | 2/2000 | Farascioni |
| 6,050,955 A | 4/2000 | Bryan et al. |
| 6,061,446 A | 5/2000 | Lester et al. |
| 6,077,230 A | 6/2000 | Gregoire et al. |
| 6,080,113 A | 6/2000 | Heneveld et al. |
| 6,083,193 A * | 7/2000 | Kadziauskas ....... A61F 9/00745 604/118 |
| 6,086,544 A | 7/2000 | Hibner et al. |
| 6,096,042 A | 8/2000 | Herbert |
| 6,106,512 A | 8/2000 | Cochran et al. |
| 6,120,462 A | 9/2000 | Hibner et al. |
| 6,120,733 A | 9/2000 | Goodman et al. |
| 6,142,955 A | 11/2000 | Farascioni et al. |
| 6,142,956 A | 11/2000 | Kortenbach et al. |
| 6,162,187 A | 12/2000 | Buzzard et al. |
| 6,213,957 B1 | 4/2001 | Milliman et al. |
| 6,228,055 B1 | 5/2001 | Foerster et al. |
| 6,231,522 B1 | 5/2001 | Voegele et al. |
| 6,245,084 B1 | 6/2001 | Mark et al. |
| 6,273,862 B1 | 8/2001 | Privitera et al. |
| 6,346,107 B1 | 2/2002 | Cucin |
| 6,402,701 B1 | 6/2002 | Kaplan et al. |
| 6,409,970 B1 | 6/2002 | Phifer |
| 6,428,487 B1 | 8/2002 | Burdorff et al. |
| 6,432,065 B1 | 8/2002 | Burdorff et al. |
| 6,485,436 B1 | 11/2002 | Truckai et al. |
| 6,544,194 B1 | 4/2003 | Kortenbach et al. |
| 6,585,664 B2 | 7/2003 | Burdorff et al. |
| 6,592,530 B1 | 7/2003 | Farhadi |
| 6,602,227 B1 | 8/2003 | Cimino et al. |
| 6,620,111 B2 | 9/2003 | Stephens et al. |
| 6,626,849 B2 | 9/2003 | Huitema et al. |
| 6,638,235 B2 | 10/2003 | Miller et al. |
| 6,659,338 B1 | 12/2003 | Dittmann et al. |
| 6,709,241 B2 | 3/2004 | Sabini et al. |
| 6,712,774 B2 | 3/2004 | Voegele et al. |
| 6,749,576 B2 | 6/2004 | Bauer |
| 6,752,768 B2 | 6/2004 | Burdorff et al. |
| 6,758,824 B1 | 7/2004 | Miller et al. |
| 6,849,080 B2 | 2/2005 | Lee et al. |
| 6,887,209 B2 | 5/2005 | Kadziauskas et al. |
| 6,904,305 B2 | 6/2005 | Tsekos |
| 6,923,809 B2 | 8/2005 | Eggers et al. |
| 6,993,375 B2 | 1/2006 | Burbank et al. |
| 6,996,433 B2 | 2/2006 | Burbank et al. |
| 6,996,443 B2 | 2/2006 | Marshall et al. |
| 7,001,341 B2 | 2/2006 | Gellman et al. |
| 7,025,098 B2 | 4/2006 | Osborne |
| 7,025,732 B2 | 4/2006 | Thompson et al. |
| 7,047,063 B2 | 5/2006 | Burbank et al. |
| 7,053,586 B2 | 5/2006 | Jones |
| 7,108,660 B2 | 9/2006 | Stephens et al. |
| 7,153,274 B2 | 12/2006 | Stephens et al. |
| 7,156,815 B2 | 1/2007 | Leigh et al. |
| 7,226,424 B2 | 6/2007 | Ritchart et al. |
| 7,229,439 B2 | 6/2007 | Burbank et al. |
| 7,252,641 B2 | 8/2007 | Thompson et al. |
| 7,276,032 B2 | 10/2007 | Hibner |
| 7,372,510 B2 | 5/2008 | Abileah |
| 7,419,472 B2 | 9/2008 | Hibner et al. |
| 7,438,692 B2 | 10/2008 | Tsonton et al. |
| 7,442,171 B2 | 10/2008 | Stephens et al. |
| 7,465,279 B2 | 12/2008 | Beckman et al. |
| 7,488,295 B2 | 2/2009 | Burbank et al. |
| 7,517,322 B2 | 4/2009 | Weikel, Jr. et al. |
| 7,641,668 B2 | 1/2010 | Perry et al. |
| 7,645,240 B2 | 1/2010 | Thompson et al. |
| 7,736,382 B2 | 6/2010 | Webb et al. |
| 7,740,597 B2 | 6/2010 | Cicenas et al. |
| 7,753,857 B2 | 7/2010 | Hibner |
| 7,758,515 B2 | 7/2010 | Hibner |
| 7,769,426 B2 | 8/2010 | Hibner et al. |

(56) References Cited

U.S. PATENT DOCUMENTS

| | | |
|---|---|---|
| 7,806,834 B2 | 10/2010 | Beckman et al. |
| 7,806,835 B2 | 10/2010 | Hibner et al. |
| 7,826,883 B2 | 11/2010 | Hibner et al. |
| 7,828,748 B2 | 11/2010 | Hibner |
| 7,846,107 B2 | 12/2010 | Hoffman et al. |
| 7,854,706 B2 | 12/2010 | Hibner |
| 7,854,707 B2 | 12/2010 | Hibner et al. |
| 7,867,173 B2 | 1/2011 | Hibner et al. |
| 7,871,384 B2 | 1/2011 | Thompson et al. |
| 7,896,817 B2 | 3/2011 | Garrison |
| 7,914,464 B2 | 3/2011 | Burdorff et al. |
| 7,918,804 B2 | 4/2011 | Monson et al. |
| 7,938,786 B2 | 5/2011 | Ritchie et al. |
| 8,002,713 B2 | 8/2011 | Heske et al. |
| 8,016,772 B2 | 9/2011 | Heske et al. |
| 8,105,849 B2 | 1/2012 | McDevitt et al. |
| 8,109,885 B2 | 2/2012 | Heske et al. |
| 8,109,886 B2 | 2/2012 | Miller et al. |
| 8,118,755 B2 | 2/2012 | Hibner et al. |
| 8,172,773 B2 | 5/2012 | Heske et al. |
| 8,206,316 B2 | 6/2012 | Hibner et al. |
| 8,226,677 B2 | 7/2012 | Kauker et al. |
| 8,251,916 B2 | 8/2012 | Speeg et al. |
| 8,376,957 B2 | 2/2013 | Hibner et al. |
| 8,414,605 B2 | 4/2013 | Gordon et al. |
| 8,454,531 B2 | 6/2013 | Speeg et al. |
| 8,480,595 B2 | 7/2013 | Speeg et al. |
| 8,764,680 B2 | 7/2014 | Rhad et al. |
| 8,801,742 B2 | 8/2014 | Rhad et al. |
| 8,858,465 B2 | 10/2014 | Fiebig |
| 8,932,233 B2 | 1/2015 | Haberstich et al. |
| 8,938,285 B2 | 1/2015 | Fiebig et al. |
| 2001/0014776 A1 | 8/2001 | Oriol et al. |
| 2002/0120212 A1 | 8/2002 | Ritchart et al. |
| 2003/0161816 A1* | 8/2003 | Fraser ............. C12N 5/0667 424/93.7 |
| 2003/0199753 A1 | 10/2003 | Hibner et al. |
| 2005/0004559 A1 | 1/2005 | Quick et al. |
| 2005/0049521 A1 | 3/2005 | Miller et al. |
| 2005/0075581 A1 | 4/2005 | Schwindt |
| 2005/0082518 A1 | 4/2005 | Kunitz |
| 2005/0256445 A1 | 11/2005 | Cucin |
| 2006/0074345 A1 | 4/2006 | Hibner |
| 2006/0085759 A1 | 4/2006 | Knapheide |
| 2006/0282012 A1 | 12/2006 | McAlister et al. |
| 2007/0010738 A1 | 1/2007 | Mark et al. |
| 2007/0055173 A1 | 3/2007 | DeLonzor et al. |
| 2007/0191732 A1 | 8/2007 | Voegele |
| 2008/0004545 A1 | 1/2008 | Garrison |
| 2008/0214955 A1 | 9/2008 | Speeg et al. |
| 2008/0221479 A1 | 9/2008 | Ritchie et al. |
| 2008/0228103 A1* | 9/2008 | Ritchie ............. A61B 10/0275 600/563 |
| 2009/0131821 A1 | 5/2009 | Speeg et al. |
| 2009/0192408 A1 | 7/2009 | Mark |
| 2010/0152610 A1 | 6/2010 | Parihar et al. |
| 2010/0152611 A1* | 6/2010 | Parihar ............. A61B 10/0275 600/566 |
| 2010/0152615 A1* | 6/2010 | Mark ............. A61B 10/0275 600/567 |
| 2010/0160819 A1 | 6/2010 | Parihar et al. |
| 2012/0116246 A1 | 5/2012 | Hibner et al. |
| 2013/0053724 A1 | 2/2013 | Fiebig et al. |
| 2013/0324882 A1 | 12/2013 | Mescher |
| 2014/0039343 A1 | 2/2014 | Mescher et al. |

FOREIGN PATENT DOCUMENTS

| | | |
|---|---|---|
| CN | 1753646 A | 3/2006 |
| CN | 101301213 A | 11/2008 |
| CN | 101502427 A | 8/2009 |
| CN | 104334089 A | 2/2015 |
| DE | 4212910 | 10/1993 |
| EP | 0 178 507 | 4/1986 |
| EP | 0 262 670 | 6/1988 |
| EP | 0 378 692 | 7/1990 |
| EP | 1 074 271 | 2/2001 |
| EP | 1 040 790 | 10/2002 |
| EP | 1 815 815 | 8/2007 |
| EP | 1 832 234 | 9/2007 |
| EP | 1 932 481 | 6/2008 |
| EP | 2 062 535 | 5/2009 |
| EP | 2 062 537 | 5/2009 |
| EP | 2 412 314 | 2/2012 |
| GB | 2 018 601 | 10/1979 |
| GB | 2 191 585 | 12/1987 |
| WO | WO 1990/08508 | 8/1990 |
| WO | WO 1993/14707 | 8/1993 |
| WO | WO 1995/25465 | 9/1995 |
| WO | WO 1997/24991 | 7/1997 |
| WO | WO 1998/06338 | 2/1998 |
| WO | WO 1998/25556 | 6/1998 |
| WO | WO 2003/077768 | 9/2003 |
| WO | WO 2004/075728 | 9/2004 |
| WO | WO 2006/005342 | 1/2006 |
| WO | WO 2007/019152 | 2/2007 |
| WO | WO 2007/112751 | 10/2007 |
| WO | WO 2013/181005 A1 | 12/2013 |

OTHER PUBLICATIONS

Chinese Office Action dated Mar. 30, 2017 for Application No. CN 2013800276960, 9 pages.

Chinese Office Action dated Jan. 29, 2016 for Application No. CN 2013800276960.

European Search Report and Written Opinion dated Dec. 20, 2007 for Application No. 07253220.

European Search Report and Written Opinion dated Mar. 10, 2009 for Application No. 08253776.

European Search Report and Written Opinion dated Mar. 9, 2009 for Application No. 08253774.

European Search Report and Written Opinion dated Mar. 9, 2009 for Application No. EP 08253775.

European Search Report and Written Opinion dated Mar. 9, 2009 for Application No. EP 08253781.

Supplementary European Search Report and Written Opinion dated Jan. 11, 2016 for Application No. EP 13796714.

International Search Report dated Jul. 18, 2007 for Application No. PCT/US2006/030022.

International Preliminary Report on Patentability and Written Opinion dated Feb. 5, 2008 for Application No. PCT/US2006/030022.

International Search Report and Written Opinion dated Aug. 19, 2013 for Application No. PCT/US2013/041784.

EnCor MRI Specifications and Breast Biopsy System, SenoRx (2005) p. 102.

Mamotome MR Biopsy System Operator's Manual, Ethicon Endo-Surgery, Inc., Cincinnati, Ohio (2006) pp. 1-86.

Defendants' Preliminary Invalidity Contentions, dated Apr. 25, 2008, Ethicon *Endo-Surgery, Inc.* v. *Hologic, Inc, et al.*; Case No. 1:07-cv-00834; US District Court, Southern District of Ohio.

Defendants' Supplemental Preliminary Invalidity Contentions, dated Jul. 25, 2008, Ethicon *Endo-Surgery, Inc.* v. *Hologic, Inc., et al.*; Case No. 1:07-cv-00834; US District Court, Southern District of Ohio.

Defendants' Third Supplemental Preliminary Invalidity Contentions, dated Dec. 1, 2008, Ethicon *Endo-Surgery, Inc.* v. *Hologic, Inc, et al.*; Case No. 1:07-cv-00834; US District Court, Southern District of Ohio.

Defendants' Final Invalidity Contentions, dated Sep. 11, 2009, Ethicon *Endo-Surgery, Inc.* v. *Hologic, Inc., et al.*; Case No. 107-cv-00834; US District Court, Southern District of Ohio.

Defendants' Identification of Prior Art, dated Dec. 31, 2009, *Ethicon Endo-Surgery, Inc.* v. *Hologlc, Inc., et al.*; Case No. 107-cv-00834; US District Court, Southern District of Ohio.

Transcript of Testimony by Dr. David Lipson on Feb. 12, 2010, at trial; *Ethicon Endo-Surgery, Inc.* v. *Hologic, Inc, et al.*; Case No. 1:07-cv-00834; US District Court, Southern District of Ohio.

(56) References Cited

OTHER PUBLICATIONS

Parker et al., "From the RSNA Refresher Courses: Performing a Breast Biopsy with a Directional, Vacuum-assisted Biopsy Instrument," *RadioGraphics 1997*; 17 (RSNA 1997) pp. 1233-1252.
Parker, et al., "Stereotactic Breast Biopsy with 3 Biopsy Gun," Radiology 1990; 176 (RSNA1990) pp. 741-747.
Van Berkel, C., "55.1: 3D Touchless Display Interaction," SID 02 Digest, pp. 1410-1413.
U.S. Appl. No. 60/869,736, filed Dec. 13, 2006.
U.S. Appl. No. 60/874,792, filed Dec. 13, 2006.
U.S. Appl. No. 61/566,793, filed Dec. 5, 2011.
Chinese Office Action dated Sep. 20, 2016 for Application No. CN 2013800276960, 2 pages.
Chinese Office Action dated Oct. 9, 2016 for Application No. CN 2013800276960, 7 pages.
U.S. Appl. No. 13/483,235; and.
U.S. Appl. No. 13/964,202.

\* cited by examiner

CONTROL FOR BIOPSY DEVICE

This application is a divisional of U.S. application Ser. No. 13/483,235, filed May 30, 2012, published as U.S. Pub. No. 2013/0324882 on Dec. 5, 2013, entitled "Control for Biopsy Device," the disclosure of which is incorporated by reference herein.

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pat. No. 6,626,849, entitled "MRI Compatible Surgical Biopsy Device," issued Sep. 11, 2003; U.S. Pat. No. 7,442,171, entitled "Remote Thumbwheel for a Surgical Biopsy Device," issued Oct. 8, 2008; U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; U.S. Pat. Pub. No. 2006/0074345, entitled "Biopsy Apparatus and Method," published Apr. 6, 2006; U.S. Pat. Pub. No. 2008/0214955, entitled "Presentation of Biopsy Sample by Biopsy Device," published Sep. 4, 2008; U.S. Pat. Pub. No. 2008/0221480, entitled "Biopsy Sample Storage," published Sep. 11, 2008; U.S. Pat. Pub. No. 2009/0131821, entitled "Graphical User Interface For Biopsy System Control Module," published May 21, 2009; U.S. Pat. Pub. No. 2009/0131820, entitled "Icon-Based Uswer Interface On Biopsy System Control Module," published May 21, 2009; U.S. Pat. Pub. No. 2010/0152610, entitled "Hand Actuated Tetherless Biopsy Device with Pistol Grip," published Jun. 17, 2010; U.S. Pat. Pub. No. 2010/0160819, entitled "Biopsy Device with Central Thumbwheel," published Jun. 24, 2010; U.S. Pat. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; U.S. Non-Provisional patent application Ser. No. 13/086,567, entitled "Biopsy Device with Motorized Needle Firing," filed Apr. 14, 2011; U.S. Non-Provisional patent application Ser. No. 13/150,950, entitled "Needle Assembly and Blade Assembly for Biopsy Device," filed Jun. 1, 2011; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; and U.S. Provisional Patent App. No. 61/566,793, entitled "Biopsy Device With Slide-In Probe," filed Dec. 5, 2011. The disclosure of each of the above-cited U.S. patents, U.S. patent application Publications, and U.S. Non-Provisional patent applications is incorporated by reference herein.

While several systems and methods have been made and used for obtaining a biopsy sample, it is believed that no one prior to the inventor has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
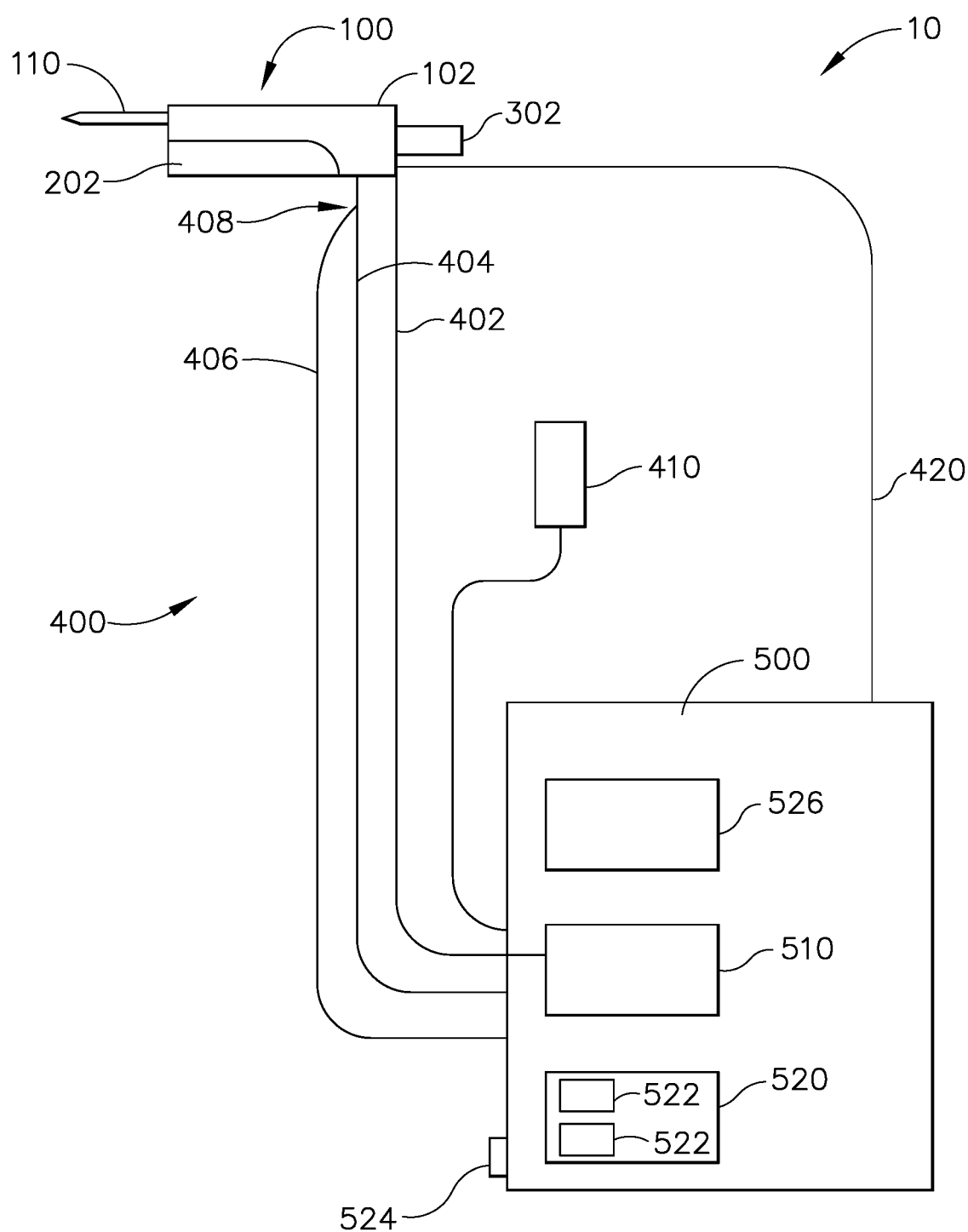
FIG. 1 depicts a schematic view of an exemplary biopsy system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Biopsy System

FIG. 1 depicts an exemplary biopsy system (10) comprising a biopsy device (100), a plurality of conduits (400) and a control module (500). Biopsy device (100) comprises a holster (202) and a probe (102). A needle (110) extends distally from probe (102) and is inserted into a patient's tissue to obtain tissue samples as will be described in greater detail below. These tissue samples are deposited into a tissue sample holder (302) that is coupled to a proximal end of probe (102), as will also be describe in further detail below. Of course needle (110) and tissue sample holder (302) may be coupled to probe (102) at a range of locations. For instance, needle (110) may extend from the top of probe (102), from a side of probe (102), from the bottom of probe (102), or, may be omitted from probe (102) entirely. Tissue sample holder (302) may be coupled to the top of probe (102), to a side of probe (102), to the bottom of probe (102), or, may be omitted from probe (102) entirely. Probe (102) of the present example is separable from holster (202), though this is merely optional. It should also be understood that the use of the term "holster" herein should not be read as necessarily requiring any portion of probe (102) to be inserted into any portion of holster (202). While an notched upper control unit (220) of the holster (202) and a latch (190) of probe (102) are used to cooperatively removably secure probe (102) to holster (202), as shown in FIGS. 2-4 and 7 and described in greater detail below, it should be understood that a variety of other types of structures, components, features, etc. (e.g., bayonet mounts, prongs, clamps, clips, snap fittings, etc.) may be used to provide removable coupling of probe (102) and holster (202). Furthermore, in some biopsy devices (100), probe (102) and holster (202) may be of unitary or integral construction, such that the two components cannot be separated. By way of example only, in versions where probe (102) and holster (202) are provided as separable components, probe (102) may be provided as a disposable component, while holster (202) may be provided as a reusable component. Still other suitable structural and functional relationships between probe (102) and holster (202) will be apparent to those of ordinary skill in the art in view of the teachings herein.

Biopsy system (10) shown in FIG. 1 further includes a control module (500) that is fluidly coupled to biopsy device (100) via one or more conduits (400). In the present example, control module (500) comprises a vacuum source (510) operable to provide a vacuum to biopsy device (100). Control module (500) further comprises a user interface (526) that allows a user adjust the level of vacuum provided to biopsy device (100). It may be desirable for a user to adjust the level of vacuum depending on the characteristics (hardness, thickness, etc.) of the tissue to be sampled by biopsy device (100). User interface (526) will be discussed in more detail below. By way of example only, vacuum source (510) is contained within control module (500) and is fluidly coupled to probe (102) via a first conduit (402), such as flexible tubing. Of course, in addition or in the alternative, vacuum source (510) may be incorporated into probe (102), incorporated into holster (202), and/or be a separate component altogether. One merely exemplary biopsy device (100) having a vacuum source (510) incorporated therein is disclosed in U.S. Non-provisional patent application Ser. No. 12/953,715, entitled "Handheld Biopsy Device with Needle Firing," filed Nov. 24, 2010, the disclosure of which is incorporated by reference herein. As shown in FIG. 1, vacuum source (510) is in fluid communication with probe (102) and, as will be described in greater detail below, with needle (110). Thus, vacuum source (510) may be activated to draw tissue into a lateral aperture (112) of needle (110), described in more detail below. Vacuum source (510) is also in fluid communication with tissue sample holder (302) and a cutter (120). Vacuum source (510) of control module (500) may thus also be activated to draw severed tissue samples through a cutter lumen (136) of cutter (120) and into tissue sample holder (302). Of course other suitable configurations and uses for vacuum source (510) will be apparent to those of ordinary skill in the art in view of the teachings herein. It should also be understood that vacuum source (510) may simply be omitted, if desired.

In some versions, vacuum source (510) is provided in accordance with the teachings of U.S. Pat. Pub. No. 2008/0214955, entitled "Presentation of Biopsy Sample by Biopsy Device," published Sep. 4, 2008, the disclosure of which is incorporated by reference herein. As yet another merely illustrative example, vacuum source (510) may be provided in accordance with the teachings of U.S. Pat. Pub. No. 2011/0208069, entitled "Biopsy Device with Auxiliary Vacuum Source," published Aug. 25, 2011, the disclosure of which is incorporated by reference herein. Still other suitable ways in which vacuum source (510) may be provided will be apparent to those of ordinary skill in the art in view of the teachings herein.

A. Exemplary Control module and Conduits

Control module (500) of the present example is further fluidly coupled to biopsy device (100) by a second conduit (404) and a third conduit (406), such as flexible tubing, though one or both may be omitted. Third conduit (406) is in fluid communication with a saline bag (410) via control module (500). Saline bag (410) comprises saline fluid, though it should be understood that other fluids, gels, solids suspended in fluid, and/or other fluid-like materials may be used as will be apparent to one of ordinary skill in the art in view of the teachings herein. Of course it should be understood that saline bag (410) may be directly coupled to third conduit (406) and/or to biopsy device (100). Furthermore, in some versions, third conduit (406) is not coupled to control module (500), but may instead include a luer lock end (not shown) to which syringes (not shown) or other items may be coupled to deliver fluids, medicaments, and/or other items. Second conduit (404) is also fluidly coupled to control module (500) and provides filtered atmospheric air to the biopsy device (100) via a filter (not shown) in control module (500). As with third conduit (406), in some versions second conduit (404) is not coupled to control module (500), but and instead includes a luer lock end (not shown) or a filter (not shown). In the present example, second conduit (404) and third conduit (406) are joined together by a connector (408) prior to coupling to probe (102). Connector (408) may comprise a valve to seal either second or third conduit (404, 406) while the other conduit (404, 406) is in fluid communication with probe (102). Of course in other versions, connector (408) may comprise a Y-shaped connector to permit both second conduit (404) and third conduit (406) to be coupled to probe (102).

In some versions, conduits (400) may be coupled to a retraction system (520) of control module (500) such that first, second, and/or third conduit (402, 402, 406) may be retracted into control module (500) when not in use. By way of example only, retraction system (520) may comprise one or more spring-loaded spools (522) each sized to coil first, second, and/or third conduit (402, 404, 406) about spools (522). Spools (522) may be coupled to a ratchet assembly (not shown) such that when a user pulls on conduits (402, 404, 406), the ratchet assembly prevents spring-loaded spools from retracting conduits (402, 404, 406). A retraction button (524) is mounted to a casing of control module (500) and is operable to release the ratchet assembly to retract conduits (402, 404, 406). In addition, or in the alternative, spools (522) may be coupled to hand cranks (not shown) to manually retract conduits (402, 404, 406) about spools (522). In some versions, retraction button (524) is operated from biopsy device (100), for example, by a button (228) on notched upper control unit (220), such that a user can retract conduits (402, 404, 406) while using the device. By way of example only, a button (not shown) on biopsy device (100) may activate a solenoid to release the ratchet assembly. Accordingly, the user can reduce the amount of potential tangling and/or any excess conduit (402, 404, 406) around where the user is using biopsy device (100). In addition, or in the alternative, such remote retraction may be selectively braked or controlled (either by a brake or a motor) to slowly retract the conduit (402, 404, 406). Such slowed retraction may prevent conduit (402, 404, 406) from rapidly retracting and pulling biopsy device (100) out of the user's hands.

While conduits (402, 404, 406) are shown as separate conduits, it should be understood that conduits (402, 404, 406) may be combined into a single tube subdivided into any number of suitable conduits. In some versions, conduits (402, 404, 406) may be longitudinally fused together to form a rectangular unitary three conduit tube. Of course still further configurations for conduits (402, 404, 406) will be apparent to one of ordinary skill in the art in view of the teachings herein. In some versions conduits (402, 404, 406) may not retract, or only part of conduits (402, 404, 406) may retract. In such a configuration, conduits (402, 404, 406) may be separable from a connector (not shown) operable to couple to one or more receptacles (not shown) on control module (500). Accordingly, after conduits (402, 404, 406) are used in a procedure, conduits (402, 404, 406) may be detached from the connector and disposed of. New conduits (402, 404, 406) may be coupled to the connector for the next procedure. In one merely exemplary configuration, a reusable conduit portion may be coupled to a disposable conduit portion. The reusable conduit portion of this example may be coupled to the retraction system (520). Accordingly, the reusable conduit portion may have a predetermined size, such as five feet, and one or more disposable conduits may be coupled to the reusable conduit portion to provide various lengths of conduit for a procedure. When the procedure is finished, the disposable conduit portions are disposed of and the reusable conduit portion is retracted into control module (500) for storage. In addition, or in the alternative, retraction system (520) and conduits (402, 404, 406) may be constructed as a selectively insertable device that may be inserted or removed from control module (500). By way of example only, such a selectively insertable retraction system (520) may be configured similarly to the vacuum canisters described in U.S. Pat. No. 7,938,786, entitled "Vacuum Timing Algorithm for Biopsy Device," issued May 10, 2011 the disclosure of which is incorporated by reference herein. Accordingly, in some versions the entire retraction system (520) may be disposable or, in some versions, reclaimable to be resterilized for reuse.

In the present example, a power cord (420) extends from vacuum control unit (500) to electrically couple and power biopsy device (100). Power cord (420) may be configured to supply DC or AC power to biopsy device (100). In addition, or in the alternative, power cord (420) may also be operable to transmit data between control module (500) and biopsy device (100). Power cord (420) includes an end connector (not shown) configured to selectively couple to an end connector (298) of cable (290), shown in FIGS. 2-6. Accordingly, power cord (420) of control module (500) may be separable from holster (202) such that each may be stored separately, though this is merely optional. Power cord (420) of the present example is also coupled to a spring-loaded spool (522) that may be retracted by retraction system (520) described above. It should be understood that spool (522) to which power cord (420) is coupled may be a separate spool from the spools for conduits (402, 404, 406). In addition, the retraction system (520) for spool (522) to which power cord (420) is coupled may be a separate retraction system as well. For instance, control module (500) may have a removable retraction system (520) for conduits (402, 404, 406) that may be removed and disposed of while a permanent retraction system (520) is provided for power cord (420). Of course, some versions of biopsy device (100) may be internally powered such that power cord (420) may be omitted. In some versions, spools (522) may comprise a single spool having multiple discrete spools such that conduits (402, 404, 406) and power cord (420) are retracted and extended at the same time and rate. In some versions, power cord (420) may be incorporated into the singular tube conduit described above such that a single cord, having three subdivisions for fluid flow and one subdivision to transmit power, extends from vacuum control unit (500). Still further configurations for power cord (420), control module (500), and/or retraction systems (520) will be apparent to one of ordinary skill in the art in view of the teachings herein.

B. Exemplary Biopsy Device Overview

Biopsy device (100) of the present example is configured to be held by a user against a patient and guided by an ultrasound imaging device. Of course, biopsy device (100) may instead be used under stereotactic guidance, MRI guidance, PEM guidance, BSGI guidance, or otherwise. It should also be understood that biopsy device (100) may be sized and configured such that biopsy device (100) may be operated by a single hand of a user. In particular, a user may grasp biopsy device (100), insert needle (110) into a patient's breast, and collect one or a plurality of tissue samples from within the patient's breast, all with just using a single hand. Alternatively, a user may grasp biopsy device (100) with more than one hand and/or with any desired assistance. In some settings, the user may capture a plurality of tissue samples with just a single insertion of needle (110) into the patient's breast. Such tissue samples may be pneumatically deposited in tissue sample holder (302), and later retrieved from tissue sample holder (302) for analysis. While examples described herein often refer to the acquisition of biopsy samples from a patient's breast, it should be understood that biopsy device (100) may be used in a variety of other procedures for a variety of other purposes and in a variety of other parts of a patient's anatomy (e.g., prostate, thyroid, etc.). Various exemplary components, features, configurations, and operabilities of biopsy device (100) will be described in greater detail below; while other suitable components, features, configurations, and operabilities will be apparent to those of ordinary skill in the art in view of the teachings herein.

Biopsy device (100) of the present example comprises a separable probe (102) and holster (202) as shown in FIGS. 2-6. In the present example, probe (102) is configured to initially slide onto holster (202) laterally until a distal probe portion (120) enters and abuts a portion of notched upper control unit (220), then probe (102) is slid distally to secure probe (102) to holster (202). Once slide distally, latch (190) of probe (102) engages a latch member (238) of holster (202) to securely couple probe (102) to holster (202). Tissue may then be severed and transported proximally into tissue sample holder (302). Biopsy device (100) and tissue sample holder (302) may be further constructed in accordance with at least some of the teachings of U.S. Pat. No. 7,938,786, entitled "Vacuum Timing Algorithm for Biopsy Device," issued May 10, 2011; U.S. Pat. Pub. No. 2008/0221480, entitled "Biopsy Sample Storage," published Sep. 11, 2008; U.S. Pat. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; U.S. Non-Provisional patent application Ser. No. 13/086,567, entitled "Biopsy Device with Motorized Needle Firing," filed Apr. 14, 2011; and/or U.S. Non-Provisional patent application Ser. No. 13/205, 189, entitled "Access Chamber and Markers for Biopsy Device," filed Aug. 8, 2011, the disclosures of which are incorporated by reference herein. Of course still further configurations for biopsy system (10) will be apparent to one of ordinary skill in the art in view of the teachings herein.

II. Exemplary Holster

Holster (202) comprises a top housing cover (210), a housing base (260), and a cable (290). Cable (290) comprises a plurality of wires (292), shown in FIG. 6, to provide power and/or control signals to various components contained within housing base (260). Cable (290) further includes an end connector (298) operable to selectively couple holster (202) to a connector of power cord (420), described above, or, in some versions, end connector (298) may be directly coupleable to control module (500). Housing base (260) comprises a biocompatible rigid plastic material, such as polycarbonate, that is molded to include a distal upwardly bending arcuate portion (262), shown in FIGS. 2-3, such that housing base (260) may be positioned closer to a patient's body during use. By way of example only, arcuate portion (262) is sized to permit a portion of a patient's anatomy, such as a breast or other part of the patient's thorax, to at least partially occupy the curved cavity formed by arcuate portion (262) such that biopsy device (100) may be readily positioned at various orientations near to the patient's body. By way of example only, the configuration of arcuate portion (262) may permit greater access to a patient's breast than might otherwise be provided by a generally rectangular or cylindrical shaped biopsy device. Arcuate portion (262) extends proximally for approximately one-fifth the length of holster (202), though this is merely optional. In some versions, arcuate portion (262) may extend proximally for approximately half, less than half, or more than half of the longitudinal length of holster (202). In addition, or in the alternative, arcuate portion (262) may comprise a padded portion (not shown), such as a gauze pad, to reduce the "mechanical" feel of arcuate portion (262) in the event that arcuate portion (262) comes into contact with the patient's skin. Still further arrangements for arcuate portion (262) will be apparent to one of ordinary skill in the art in view of the teachings herein.

Figure 3:
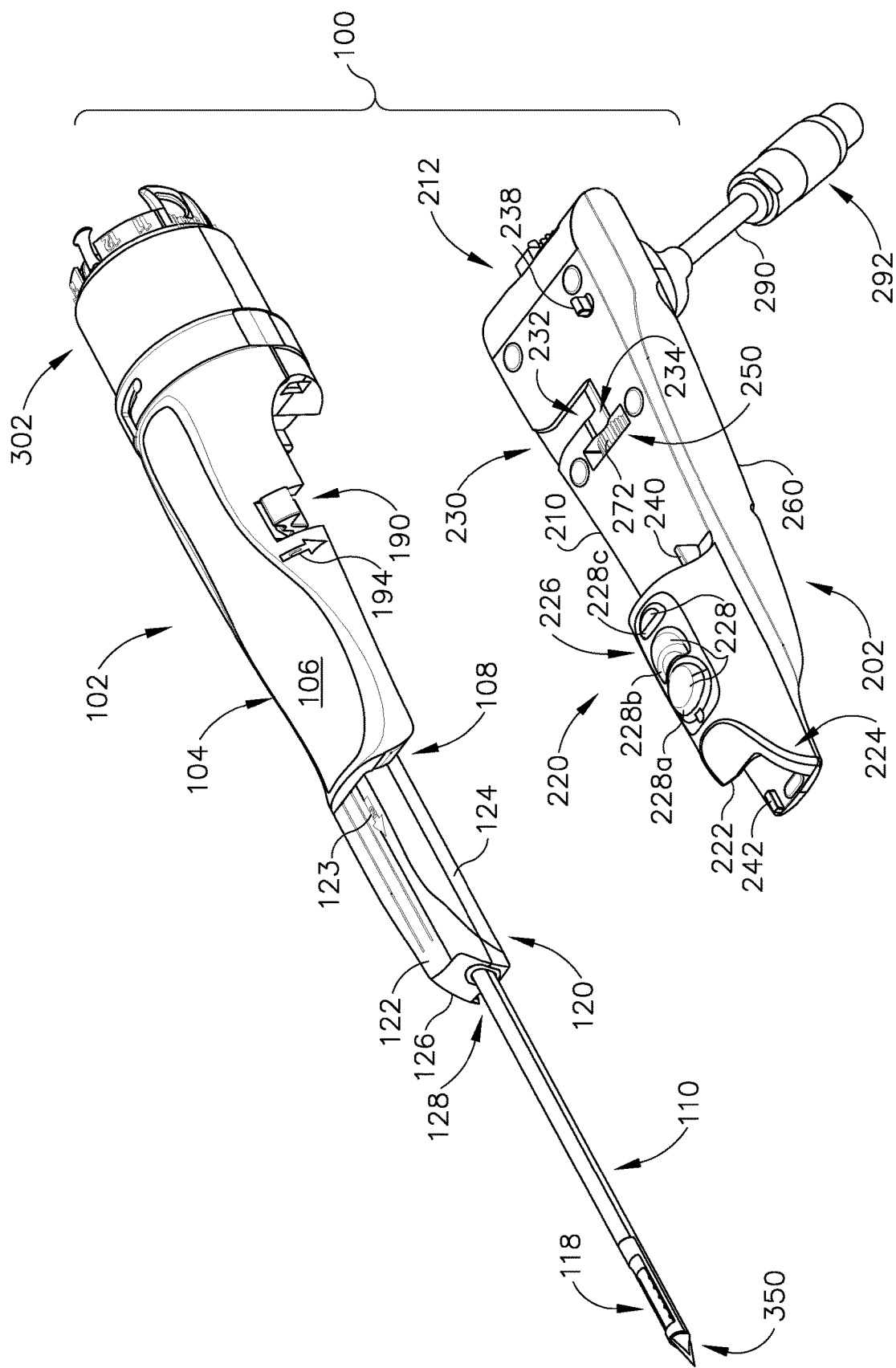
FIG. 3 depicts a perspective view of the biopsy device of FIG. 2 showing an exemplary probe decoupled from an exemplary holster.
Figure 4:
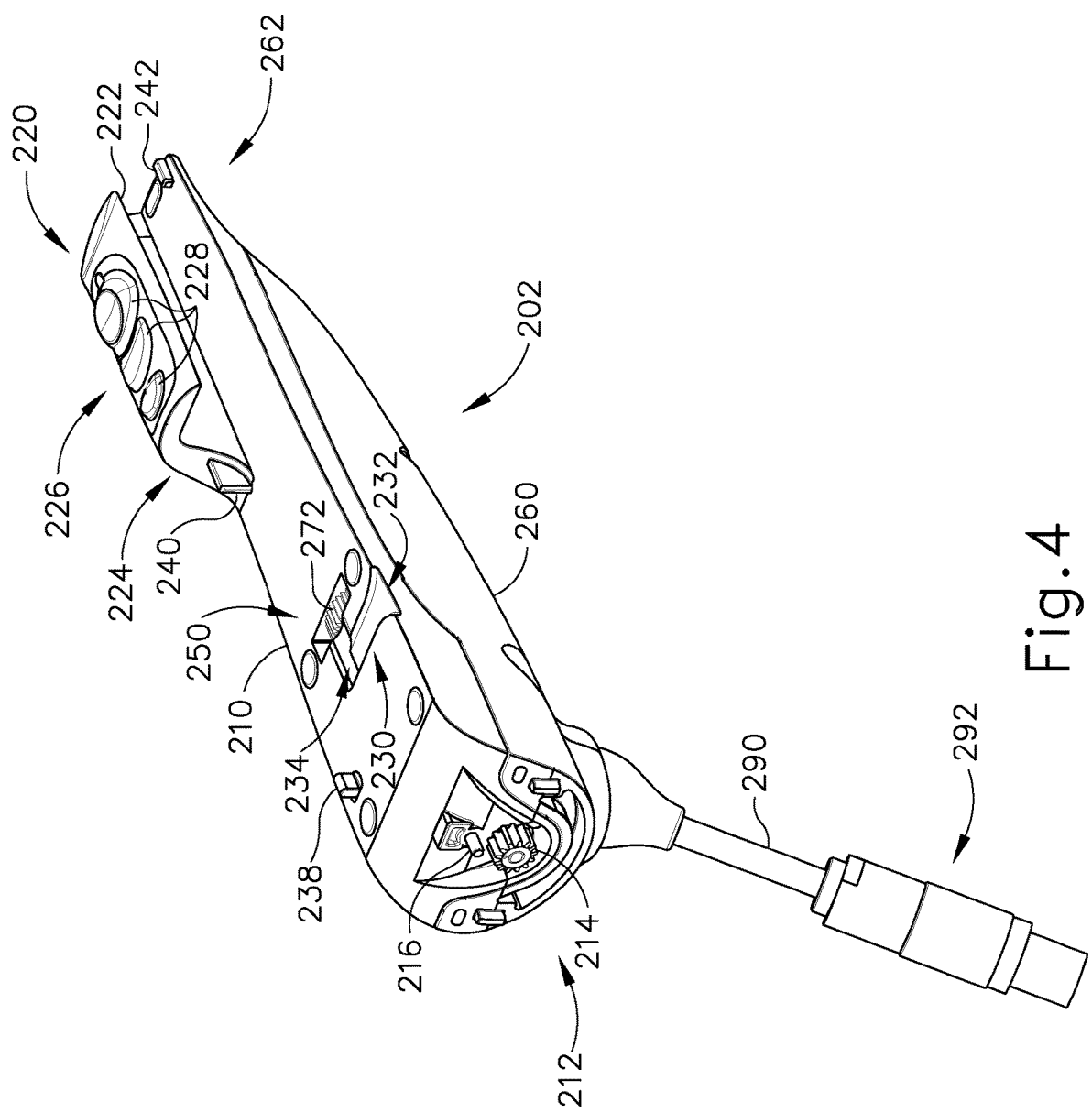
FIG. 4 depicts a rear perspective view of the holster of FIG. 3.

Referring now to FIGS. 3-4, top housing cover (210) also is formed of a biocompatible rigid plastic material, such as polycarbonate, and includes a notched upper control unit (220), a gear slot (230), a mid rail (240), a front rail (242), a latch member (238), and a gear aperture (250). As best seen in FIG. 3, holster gear (272) is exposed through gear aperture (250) and is configured to mesh with probe gear (170) of probe (102) when probe (102) is coupled to holster (202). Accordingly, rotation of holster gear (272) rotates probe gear (170) to drive a cutter actuation assembly (150) in probe (102), described in greater detail below. Gear slot (230) is a recessed portion of top housing cover (210) configured to permit probe gear (170) to travel along gear slot (230) as probe (102) is slide onto holster (202). Gear slot (230) comprises a lateral portion (232) and a longitudinal portion (234). Accordingly, when probe (102) is coupled to holster (202), probe gear (170) first enters lateral portion (232) and travels along lateral slot (232) until probe (102) is substantially longitudinally aligned with holster (202). Once probe (102) is longitudinally aligned with holster (202), probe (102) is pushed forward by the user, causing probe gear (170) to travel within longitudinal portion (234) of gear slot (230) until probe gear (170) meshes with holster gear (272). Of course gear slot (230) is merely optional and may be omitted. In addition, or in the alternative, a similar gear slot (not shown) may be formed on a bottom portion of probe (102).

As probe (102) is slid distally, a mid slot (108) of probe (102) slides onto mid rail (240) of top cover (210) and a front slot (128) slides onto front rail (242). The combination of mid slot (108), mid rail (240), front slot (128), and front rail (242) provide additional alignment for coupling probe (102) to holster (202). In addition, rails (240, 242) may also be sized such that rails (240, 242) resist lateral displacement of probe (102) relative to holster (202) once probe (102) is coupled to holster (202). Of course still further configuration for rails (240, 242) and slots (108, 128) will be apparent to one of ordinary skill in the art in view of the teachings herein.

Notched upper control unit (220) initially extends upwardly and then inwardly from a first surface of top cover (210), thereby forming an inverted L-shaped component having an overhang (222). In the example shown, notched upper control unit (220) comprises an upwardly extending portion (224) coupled to an overhang (222), thereby forming an upper boundary to secure probe (102) against holster (202). Accordingly, overhang (222) retains probe (102) against holster (202) even if biopsy device (100) is inverted or positioned in any other orientation. In addition, while notched upper control unit (220) increases the height of holster (202), it will be appreciated by one of ordinary skill in the art in view of the teachings herein that the width of holster (202) is narrowed by providing upper control unit (220). Accordingly, this narrowed width may permit a user to grasp holster (202) and/or the assembly biopsy device (100) in a similar manner to holding a pencil or other narrow-bodied object.

Notched upper control unit (220) further includes a control panel (226) having a plurality of buttons (228) thereon. In the present example, buttons (228) comprise a rocker button (228a), a first button (228b), and a second button (228c). In the present example, second button (228c) is operable to selectively activate biopsy device (100) to take a biopsy sample of tissue. First button (228b) is operable to selectively apply a vacuum from control module (500) to one or more portions of biopsy device (100), such as to cutter lumen (136). Rocker button (228a) is operable to selectively advance or retract cutter (152), thereby opening or closing lateral aperture (118). Buttons (228a, 228b, 228c) may of course have other uses, as will be apparent to one of ordinary skill in the art in view of the teachings herein. Moreover, additional buttons (228) may be provided to provide additional functionality. For instance, as noted above, one such additional button (228) may include a button to trigger retraction of conduits (402, 404, 406) and/or power cord (420) into vacuum control unit (500). In addition, or in the alternative, indicators (not shown) may be included on notched upper control unit (220) to provide visual feedback to the user. In yet a further configuration, notched upper control unit (220) may comprise a touch panel, such as a resistive touch screen, capacitive touch screen, piezoelectric touch screen, acoustic pulse recognition, and/or any other type of touch screen as will be apparent to one of ordinary skill in the art in view of the teachings herein.

As noted previously, latch member (238) engages latch (190) to selectively couple probe (102) to holster (202). In the present example, latch member (238) snaps into a gap (192), shown best in FIG. 8, of probe (102) and is secured via latch (190) when probe (102) is slid onto holster (202). When probe (102) is to be decoupled, latch (190) is depressed inwardly by a user to permit latch member (238) to clear latch (190) and exit gap (192). The user can then decouple probe (102) from holster (202).

Top cover (210) further includes a proximal end (212) having a sample holder cog (214) and a peg (216) extending proximally therefrom. Sample holder cog (214) is operable to rotate a rotatable manifold (310) of tissue sample holder (302) to rotate a plurality of tissue sample chambers into alignment with a cutter lumen (136), as will be discussed in more detail below. Peg (216) is operable to decouple a parking pawl (not shown) when probe (102) is coupled to holster (202). Sample holder cog (214) and peg (216) may be further constructed and/or configured in accordance with at least some of the teachings of U.S. Pat. No. 7,938,786, entitled "Vacuum Timing Algorithm for Biopsy Device," issued May 10, 2011 and/or U.S. Non-Provisional patent application Ser. No. 13/205,189, entitled "Access Chamber and Markers for Biopsy Device," filed Aug. 8, 2011, the disclosures of which are incorporated by reference herein.

Still further configurations for top cover (210) of holster (202) will be apparent to one of ordinary skill in the art in view of the teachings herein.

Figure 5:
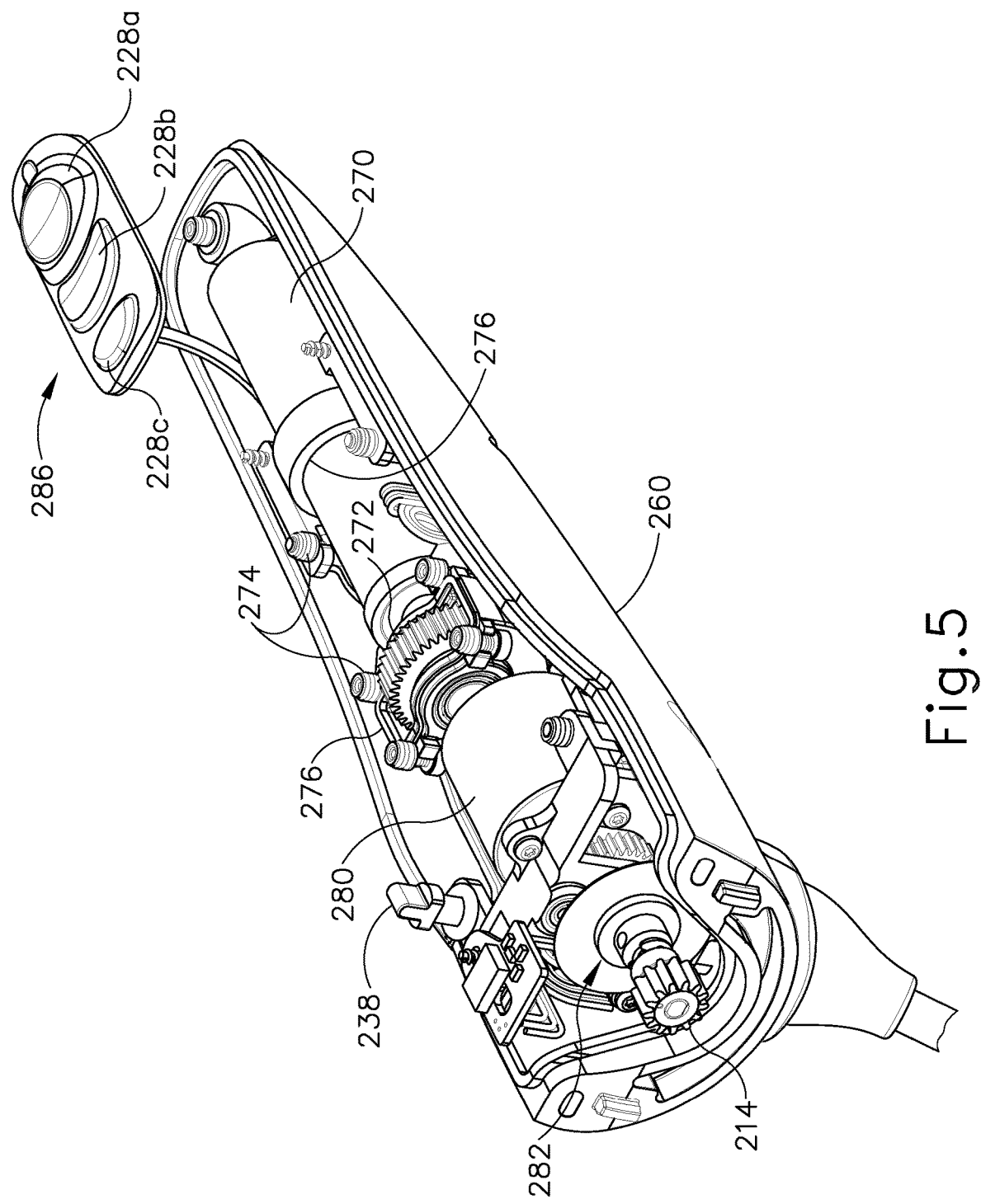
FIG. 5 depicts a rear perspective view of the holster of FIG. 4 with a top housing cover omitted.
Figure 6:
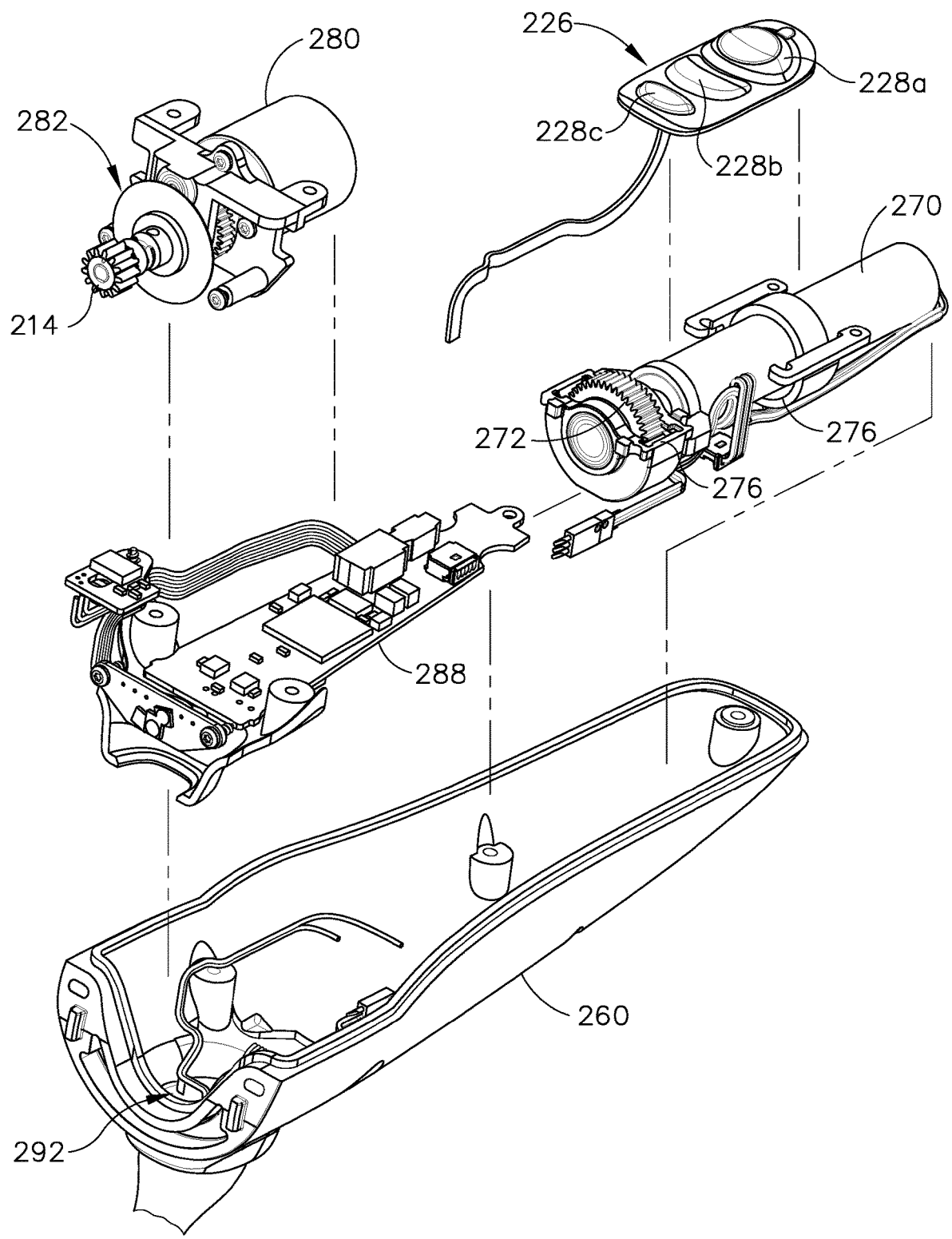
FIG. 6 depicts an exploded perspective view of the holster of FIG. 5.

FIGS. 5-6 depict holster (202) with top cover (210) removed, showing the components (270, 280, 288) contained within housing base (260). In the present example, holster (202) includes a cutter drive motor (270), a sample holder motor (280), and a controller (288). In the present example, cutter drive motor (270) is coupled to holster gear (272), a top portion of which extends out of top cover (210) through gear aperture (250). Cutter drive motor (270) is operable to engage and drive cutter actuation assembly (150) within probe (102), as will be discussed in greater detail below. In the present example, cutter drive motor (270) is mounted with one or more rubber bushings (274) and/or rubber gaskets (276) to isolate vibrations from cutter drive motor (270). Sample holder motor (280) is coupled to sample holder cog (214) and includes an encoder assembly (282) operable to transmit the rotational position of sample holder cog (214) to controller (288). Controller (288) of the present example is electrically coupled to cutter drive motor (270), sample holder motor (280), encoder assembly (282), control panel (226) and control module (500). Controller (288) is operable to output control signals to cutter drive motor (270) and/or sample holder motor (280) in response to one or more control or input signals from encoder assembly (282), control panel (226) and control module (500). Controller (288) may be further constructed or configured in accordance with at least some of the teachings of U.S. Pat. No. 7,938,786, entitled "Vacuum Timing Algorithm for Biopsy Device," issued May 10, 2011; U.S. Pat. Pub. No. 2010/0317997, entitled "Tetherless Biopsy Device with Reusable Portion," published Dec. 16, 2010; U.S. Non-Provisional patent application Ser. No. 12/953,715, entitled "Handheld Biopsy Device with Needle Firing," filed Nov. 24, 2010; and/or U.S. Non-Provisional patent application Ser. No. 13/086,567, entitled "Biopsy Device with Motorized Needle Firing," filed Apr. 14, 2011, the disclosures of which are incorporated by reference herein.

Still further constructions and/or configurations for holster (202) will be apparent to one of ordinary skill in the art in view of the teachings herein.

III. Exemplary Probe

Figure 7:
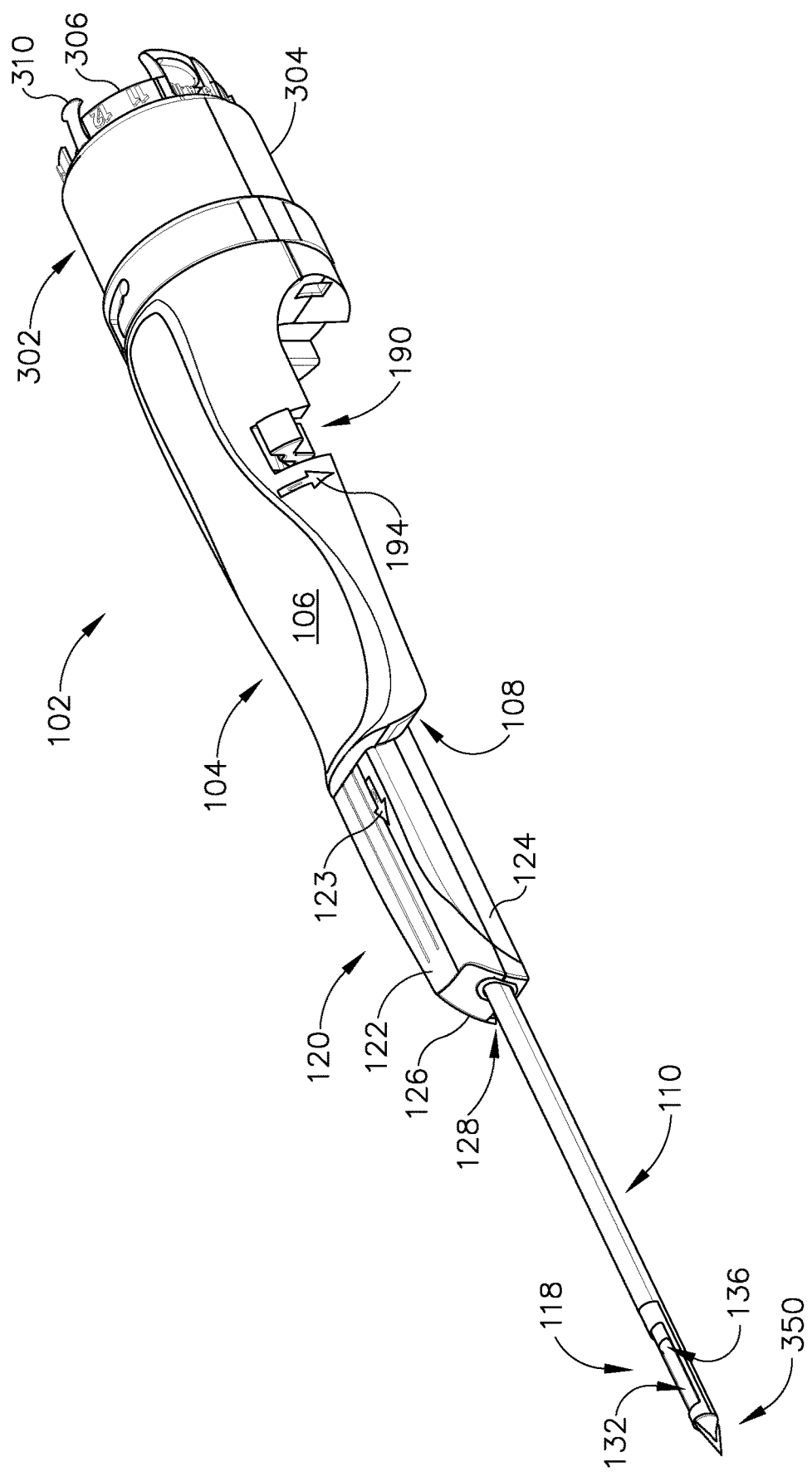
FIG. 7 depicts a perspective view of the probe of FIG. 3.
Figure 8:
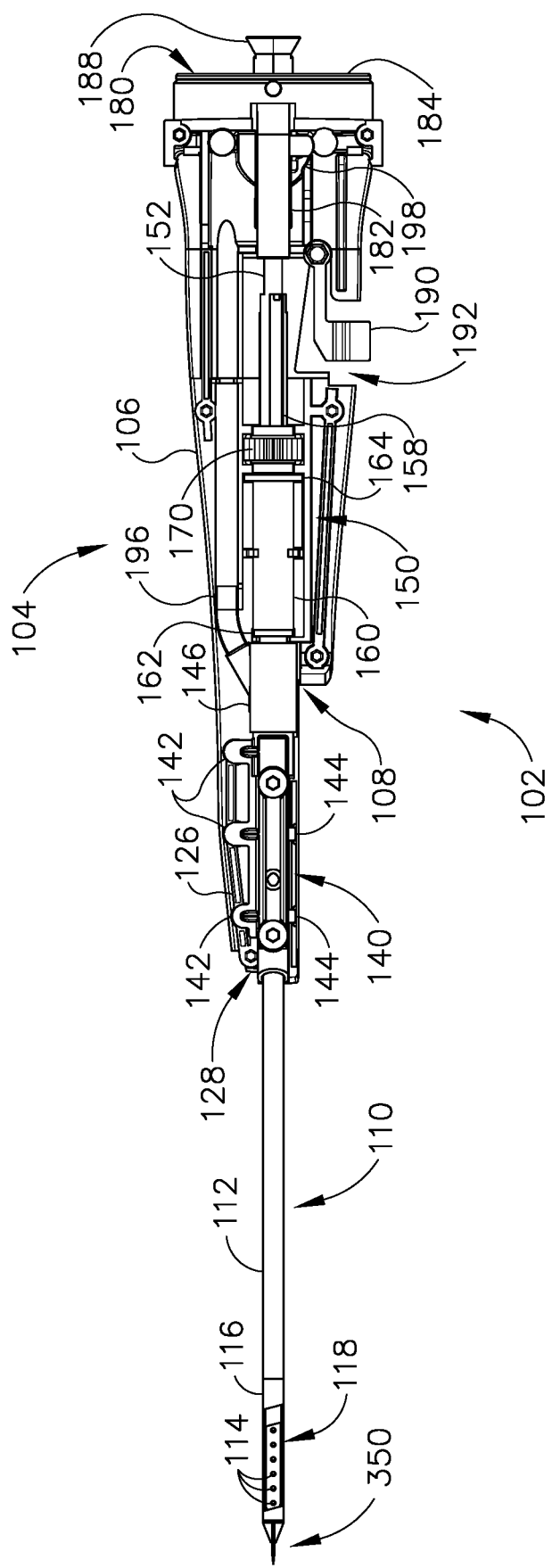
FIG. 8 depicts a top plan view of the probe of FIG. 7 with a top probe cover omitted.

FIGS. 2-3 and 7-9 depict an exemplary probe (102) configured to couple to holster (202) described above. Probe (102) of the present example comprises a probe body (104), a needle (110) extending distally from probe body (104), and a tissue sample holder (302) detachably coupled to a proximal end of probe (102). Probe body (104) of the present example comprises a biocompatible rigid plastic material, such as polycarbonate, divided into a chassis portion and a top probe cover, though this is merely optional. Indeed, in some versions, probe body (104) may be of unitary construction. As shown in FIGS. 3 and 7, probe body (104) includes a main portion (106) and a distal probe portion (120). Main portion (106) includes a mid slot (108) configured to slide onto mid rail (240) of top cover (210), as described above. Latch (190) of the present example is integrally formed as part of main portion (106), though this is merely optional and latch (190) may comprise a separate component mechanically coupled to main portion (106). As best shown in FIG. 8, latch (190) is molded such that a gap (192) receives latching member (238) of holster (202) when probe (102) is coupled to holster (202). A first indicator (194) is also included on main body (106) to indicate to the user the first step, sliding probe (102) laterally, to couple probe (102) to holster (202). Of course still other configurations and/or constructions for main portion (106) and/or latch (190) will be apparent to one of ordinary skill in the art in view of the teachings herein.

Figure 2:
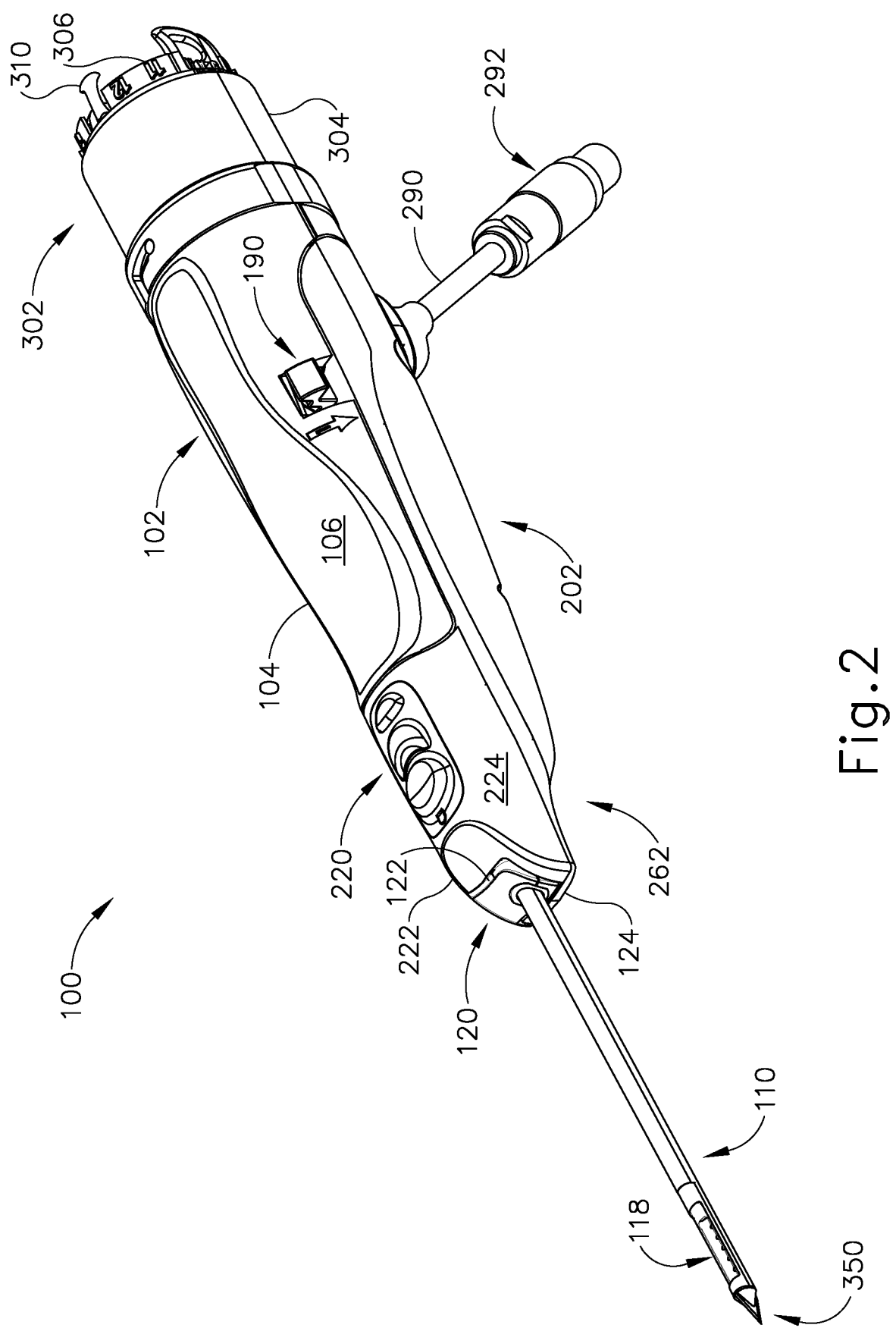
FIG. 2 depicts a perspective view of an exemplary biopsy device.

Distal probe portion (120) of the present example extends from main portion (106) and includes a top surface (122), a lateral surface (124), an outer surface (126), and a front slot (128). Top surface (122) and lateral surface (124) of the present example are formed substantially perpendicular to each other and are sized such that distal probe portion (120) nests beneath overhang (222) and adjacent to upwardly extending portion (224). Accordingly, as seen in FIG. 2, lateral surface (124) abuts upwardly extending portion (224) and top surface (122) is enclosed by overhang (222). In the present example, top surface (122) includes a second indicator (123) that instructs the user of the second step, sliding the probe longitudinally, to assemble probe (102) with holster (202). Outer surface (126) of the present example is shaped to provide a smooth transition from distal probe portion (120) to notched upper control unit (220) when probe (102) is coupled to holster (202), though this is merely optional.

Needle (110) is secured within probe body (104) by manifold (140), shown in FIG. 8, and extends distally therefrom. Needle (110) terminates with blade assembly (350) coupled to distal end (130) of needle (110). In the present example, needle (110) comprises an ovular two-piece needle having an ovular tube (112) with a notch (114) formed at a distal end of ovular tube (112) and an inset (116). Notch (114) is sized to receive inset (116) such that inset (116) and ovular tube (112) are flush at distal end (130) and form a two tiered needle having a longitudinal lumen (132)

and a lateral lumen (134). In the present example, inset (116) comprises a cylindrical tube having a plurality of openings (119) formed in a sidewall of inset (116). As will be apparent to one of ordinary skill in the art in view of the teachings herein, openings (119) allow fluid communication between lateral lumen (134) and longitudinal lumen (132). Needle (110) may be further constructed in accordance with at least some of the teachings of U.S. Non-Provisional patent application Ser. No. 13/150,950, entitled "Needle Assembly and Blade Assembly for Biopsy Device," filed Jun. 1, 2011 and/or in any other configuration as will be apparent to one of ordinary skill in the art in view of the teachings herein.

Manifold (140) of the present example receives needle (110) into an ovular aperture formed in manifold (140) to fixedly secure needle (110) into distal probe portion (120). While the present example depicts manifold (140) anchoring needle (110) within distal probe portion (120), it should be understood that manifold (140) may be anchored anywhere within probe (102). Manifold (140) further includes a plurality of hex tabs (142) and square tabs (144) to fixedly secure manifold (140) within distal probe portion (120). Hex tabs (142) include a hexagonal protrusion (not shown) extending from hex tabs (142) and configured to insert into complementary hex shaped recesses formed in distal probe portion (120) while the portion from which the hexagonal protrusions extend rests atop the framework within distal probe portion (120). Square tabs (144) insert into square recesses formed in distal probe portion (120). Accordingly, hex tabs (142) and square tabs (144) cooperatively secure manifold (140) within distal probe portion (120). It should be understood from the present example that manifold (140) substantially secures needle (110) to probe body (104) such that longer needles may be used with biopsy device (100) due to the anchoring provided by manifold (140). Of course it should be understood that manifold (140), hex tabs (142), and square tabs (144) are merely optional. By way of example only, tabs other than hex tabs (142) and/or square tabs (144) may be used, or, in some versions, manifold (140) may be integrally formed with distal probe portion (120) such that tabs (142, 144) may be omitted entirely. Still further configurations for manifold (140) will be apparent to one of ordinary skill in the art in view of the teachings herein.

Figure 9:
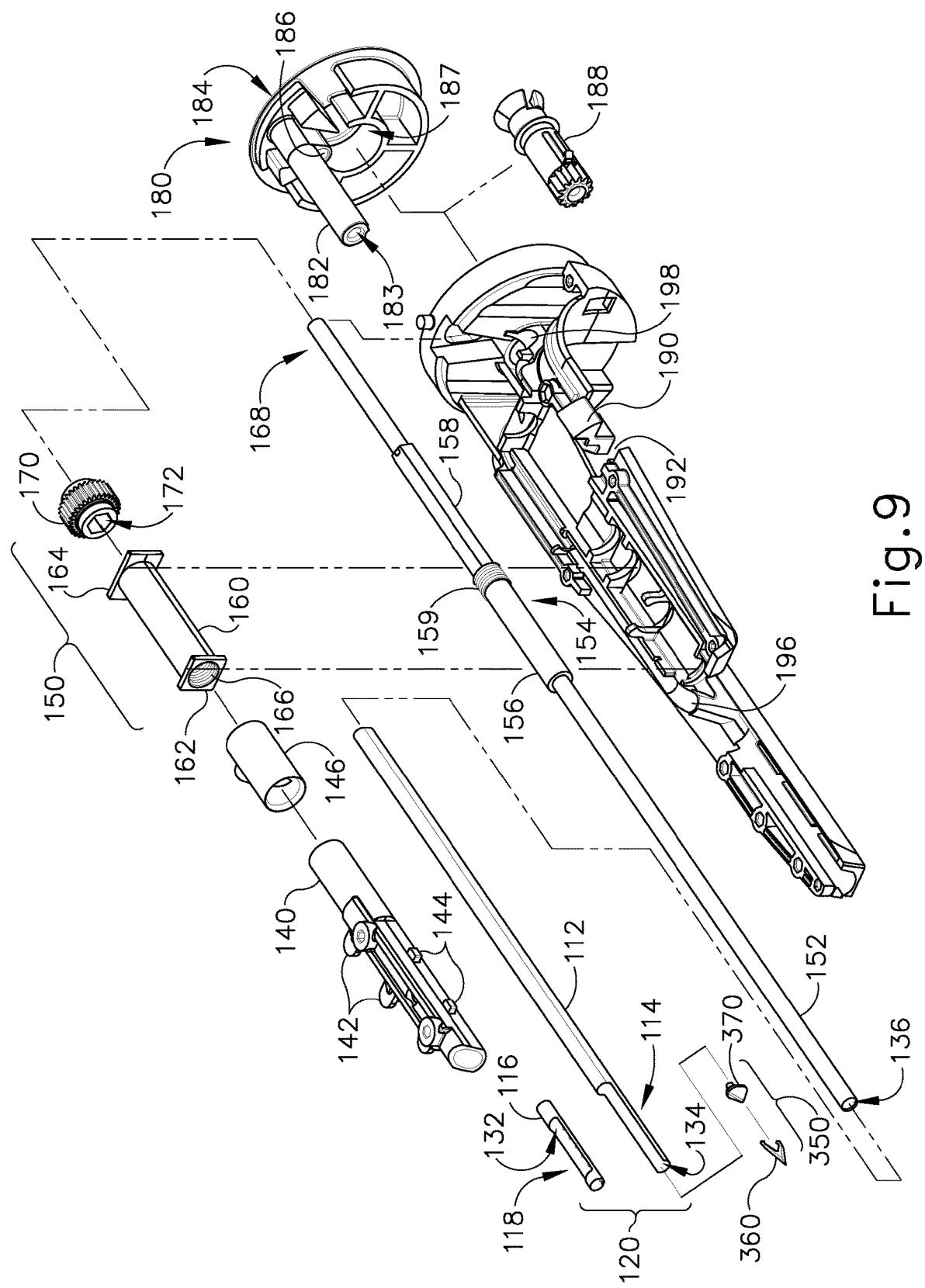
FIG. 9 depicts an exploded perspective view of the probe of FIG. 8.

In the example shown in FIGS. 8-9, a fluid junction member (146) is coupled to a proximal end of manifold (140) to fluidly couple lateral lumen (134) with one or more of conduits (400) described above. Fluid junction (146) is substantially sealed at a proximal end by distal sealing cylinder (156) of cutter overmold (154), as will be described below. Cutter (152) is inserted into inset (116) such that longitudinal lumen (132) is substantially fluidly coupled and sealed with cutter (152) and cutter lumen (136). Accordingly, the portion of ovular tube (112) extending proximally from inset (116) fluidly couples lateral lumen (134) to manifold (140) and fluid junction member (146). As seen in FIGS. 8-9, fluid junction (146) includes a Y-joint that couples fluid junction (146) to an inlet tube (196) that is subsequently coupled to one or more conduits (400), described above. By way of example only, inlet tube (196) may be selectively fluidly coupled to a vacuum source, a saline source, and/or an atmospheric source to selectively supply vacuum, saline, and/or atmospheric air through lateral lumen (134). Such selective supply of vacuum, saline, and/or atmospheric air may be controlled by control module (500) and/or through other valving assemblies, as will be apparent to one of ordinary skill in the art in view of the teachings herein. Of course other valving assemblies and/or vacuum systems may be provided in such as those disclosed in U.S. Pat. No. 7,854,706, entitled "Clutch and Valving System for Tetherless Biopsy Device," issued Dec. 1, 2010; U.S. Pat. No. 7,938,786, entitled "Vacuum Timing Algorithm for Biopsy Device," issued May 10, 2011; and/or otherwise.

As noted above, cutter (152) is inserted into inset (116) to fluidly couple cutter lumen (136) with longitudinal lumen (132). A proximal end (168) of cutter (152) is also fluidly coupled to connector tube (182) of tissue sample holder seal (180), as will be described below, thereby providing a fluid passageway for tissue to travel from longitudinal lumen (132) into tissue sample holder (302). In the present example, cutter (152) comprises an elongate tubular member having a honed distal end operable to sever tissue as cutter (152) is advanced distally within inset (116). Accordingly, when tissue is prolapsed into lateral aperture (118) (such as by providing a vacuum through lateral lumen (134)) cutter (152) may be advanced by cutter actuation assembly (150) to sever the tissue. A vacuum may then be applied through tissue sample holder (302) to draw the tissue proximally through cutter lumen (136) and into a sample holder of a tissue sample tray (306) (shown in FIGS. 2 and 7). Thus, tissue may be harvested from a location proximate to lateral aperture (118) and deposited within tissue sample holder (302). Of course tissue may be deposited at other locations, as will be apparent to one of ordinary skill in the art in view of the teachings herein.

Cutter (152) of the present example includes a cutter overmold (154) that is operable to rotate and translate cutter (152) within needle (110). In the present example, cutter overmold (154) is formed of plastic molded about cutter (152) to fixedly secure cutter overmold (154) to cutter (152), though any other suitable materials may be used, and cutter overmold (154) may be secured relative to cutter (152) using any other suitable structures or techniques (e.g., set screws, etc.). Cutter overmold (154) comprises a distal sealing cylinder (156), a proximal hex end (158) and threading (159) interposed therebetween. As noted above, distal sealing cylinder (156) is inserted into fluid junction (146) to fluidly seal the proximal end of fluid junction (146). In some versions, an o-ring (not shown) or other gasket (not shown) may be disposed about distal sealing cylinder (156) to assist in fluidly sealing the proximal end of fluid junction (146). Of course other configurations for distal sealing cylinder (156) and/or components to seal the proximal end of fluid junction (146) will be apparent to one of ordinary skill in the art in view of the teachings herein.

Threading (159) of cutter overmold (154) is configured to engage and thread into internal threading (166) of nut member (160). In the present example, nut member (160) is fixedly secured relative to probe (102) such that rotation of cutter (152) engages threading (159) and internal threading (166) to longitudinally advance or retract cutter (152) relative to needle (110) and probe (102). For instance, as shown in FIGS. 8-9, nut member (160) comprises a distal square end (162) and a proximal square end (164) each of which anchors nut member (160) to probe (102) such that nut member (160) does not rotate or translate relative to probe (102). Of course it should be understood that in some versions nut member (160) may be integrally formed or affixed to probe (102). By way of example only, threading (159, 166) may be configured to have a pitch that provides approximately 40-50 threads per inch. Such a thread pitch may provide a ratio of cutter (152) rotation to cutter (152) translation that is ideal for severing tissue. Alternatively, any other thread pitch may be used. Still further configurations of nut member (160) will be apparent to one of ordinary skill in the art in view of the teachings herein.

Cutter overmold (154) also includes a proximal hex end (158) configured to insert into and engage with hex recess (172) formed through probe gear (170). Accordingly, when probe gear (170) is rotated, the proximal hex end (158) is rotated. This rotation causes threading (159) to engage internal threading (166) of nut member (160), thereby actuating cutter (152) proximally or distally depending upon the rotation direction of probe gear (170). As noted above, probe gear (170) extends out of the bottom of probe (102) and is configured to mesh with holster gear (272). When probe (102) is coupled to holster (202), cutter drive motor (270), described above, is operable to drive cutter (152) to actuate proximally or distally as threading (159) threads within nut member (160). Hex end (158) is further configured such that cutter (152) and cutter overmold (154) may translate longitudinally relative to probe gear (170) while probe gear (170) is still operable to rotate cutter (152) and cutter overmold (154). Accordingly, probe gear (170) remains engaged with holster gear (272) while cutter (152) and cutter overmold (154) actuate longitudinally. Of course it should be understood that proximal hex end (158) and hex recess (172) are merely optional and may comprise any other complementary components that mesh to transfer rotational movement, including stars, teethed gears, squares, triangles, etc.

Figure 10:
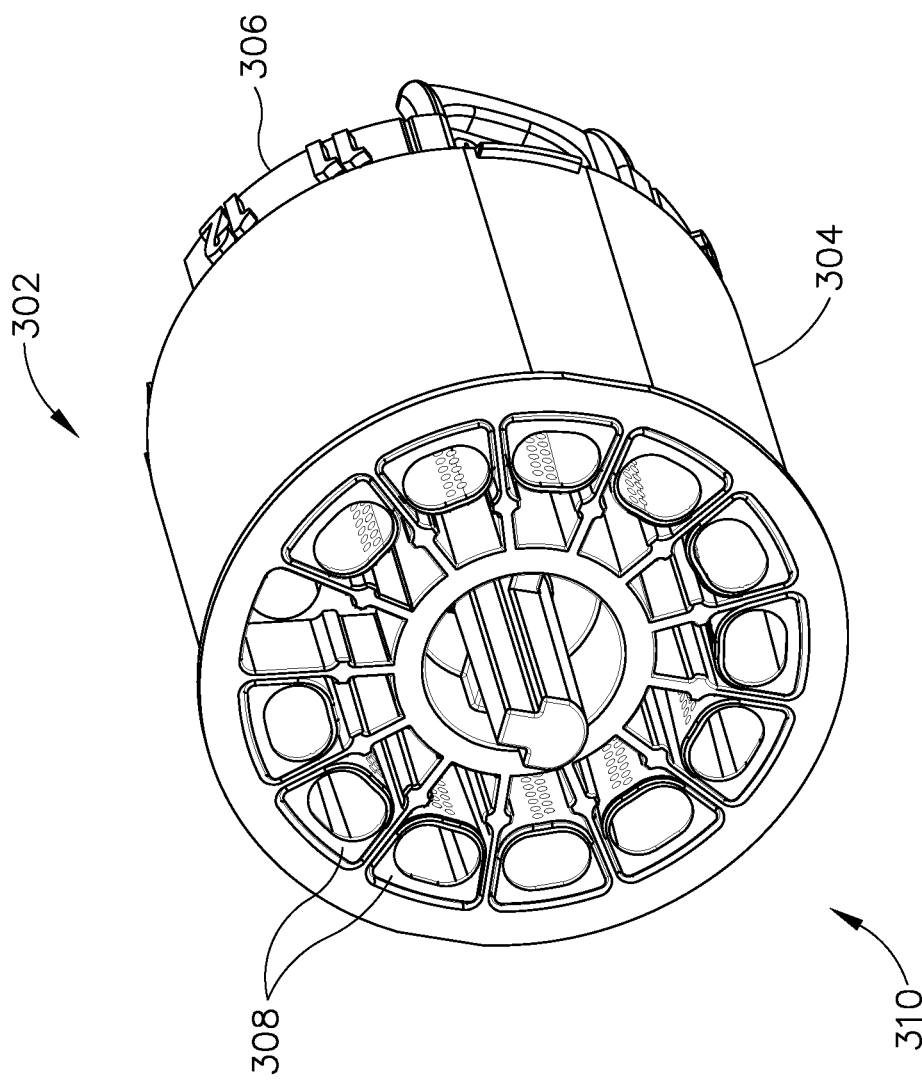
FIG. 10 depicts a perspective view of an exemplary tissue sample holder.

Tissue sample holder (302), shown in FIG. 10, is coupled to a proximal end of probe (102) and is fluidly coupled to cutter (152) such that tissue samples are transported proximally through cutter lumen (136) and into a sample holder (not shown) of tissue sample trays (306). Tissue sample holder (302) may be constructed in accordance with at least some of the teachings of U.S. Pat. No. 7,938,786, entitled "Vacuum Timing Algorithm for Biopsy Device," issued May 10, 2011; U.S. Pat. Pub. No. 2008/0221480, entitled "Biopsy Sample Storage," published Sep. 11, 2008; U.S. Non-Provisional patent application Ser. No. 13/205,189, entitled "Access Chamber and Markers for Biopsy Device," filed Aug. 8, 2011; U.S. Non-Provisional patent application Ser. No. 13/218,656, entitled "Biopsy Device Tissue Sample Holder with Bulk Chamber and Pathology Chamber," filed Aug. 26, 2011; and/or otherwise.

Tissue sample holder (302) of the present example comprises a cover (304) containing a rotatable manifold (310) with a plurality of tissue sample trays (306) inserted into rotatable manifold (310). Rotatable manifold (310) comprises a plurality of longitudinal chambers extending therethrough and annularly disposed about rotatable manifold (310). Accordingly, each chamber can be selectively aligned with cutter (152) and connector tube (182), described below, such that tissue samples can be transported from lateral aperture (118) into each chamber. Each chamber comprises an upper longitudinal tray portion and a lower fluid portion that is parallel and offset from the upper tray portion. Merely exemplary chambers are shown and described in U.S. Pat. Pub. No. 2008/0221480, entitled "Biopsy Sample Storage," published Sep. 11, 2008; U.S. Non-Provisional patent application Ser. No. 13/205,189, entitled "Access Chamber and Markers for Biopsy Device," filed Aug. 8, 2011, the disclosure of which is incorporated by reference herein. The tray portion is configured to receive a sample holder (308) of tissue sample trays (306) such that sample holder (308) is configured to receive a severed tissue sample therein. Each sample holder (308) of tissue sample trays (306) comprises a floor, a pair of sidewalls, and a proximal wall forming a cavity that is configured to receive a tissue sample therein. The floor, sidewalls, and/or proximal wall include a plurality of holes (not shown) such that fluid may be communicated from within each sample holder (308) to the lower portion of the corresponding chamber formed in the rotatable manifold. When a vacuum is applied to the lower fluid portion, the vacuum is transmitted through sample holder (308), through connector tube (182), into cutter (152) and to lateral aperture (118). Accordingly, when the vacuum is applied, a severed tissue sample is transported proximally by the vacuum into a corresponding sample holder (308). Of course other configurations for tissue sample holder (302) will be apparent to one of ordinary skill in the art in view of the teachings herein. In some versions, tissue sample trays (306) and/or sample holders (308) comprise a high-contrast color compared to the color of the tissue samples, for instance, green, red, blue, etc., such that a user may visually detect the presence of a tissue sample within tissue sample trays (306). In the example shown, a dedicated passage does not receive a sample holder (308); instead, a plug (310) is provided to selectively seal a dedicated passage.

Referring back to FIG. 9, tissue sample holder (302) is coupled to cutter (152) by a tissue sample holder seal (180). Seal (180) comprises a proximal wall (184) formed as a cylindrical disk that is configured to seal a distal end of tissue sample holder (302) to a proximal end of probe (102). By way of example only, proximal wall (184) may comprise a resilient silicon rubber disk against which tissue sample holder (302) may be compressed to form a fluid-tight seal. In some versions, proximal wall (184) may include an annular recess (not shown) sized to receive and form an interference or compression fit with a rim of tissue sample holder (302) to further seal tissue sample holder (302) to seal (180). Tissue sample holder seal (180) of the present example also includes a connector tube (182) that extends distally into probe (102) to fluidly couple to proximal end (168) of cutter (152). Connector tube (182) is integrally formed with a proximal wall (184) and includes an internal passageway (183) into which proximal end (168) of cutter (152) is inserted. In the example shown, connector tube (182) has a sufficient longitudinal length such that cutter (152) can actuate via cutter actuation assembly (150) proximally and/or distally within connector tube (182) without decoupling from connector tube (182). In the present example, connector tube (182) is configured to fluidly seal with proximal end (168) of cutter (152). By way of example only, connector tube (182) may be sized to form an interference fit with proximal end (168) of cutter (152). In addition, or in the alternative, connector tube (182) may include one or more interior seals (not shown), such as wiper seals, dome seals, domed-wiper seals, etc. to fluidly couple connector tube (182) to proximal end (168) of cutter (152).

Seal (180) also includes an aperture (186) formed through seal (180) to fluidly couple to an outlet tube (198). In the present example, aperture (186) is parallel to and offset from connector tube (182). Aperture (186) is configured to align with a lower portion of a corresponding chamber of rotatable manifold (310), described above. Outlet tube (198) is inserted into aperture (186) at a first end and is coupled to one or more conduits (400) at a second end to fluidly couple aperture (186) to the one or more conduits (400). For instance, outlet tube (198) may be coupled to a vacuum source such that a vacuum is provided through rotatable manifold (310), cutter (152), and to lateral aperture (118). In addition, or in the alternative, outlet tube (198) may be coupled to a saline source to provide saline through cutter (152) to flush the system. Further still, outlet tube (198) may be coupled to a medicine delivery system to provide medicine out of lateral aperture (118) (e.g., anti-inflammatory medicines, pain medicines, etc.).

A central opening (187) also extends through seal (180) and is configured to permit sample holder gear (188) to extend therethrough. In some versions, central opening (187) may include seals (not shown), such as wiper seals, dome seals, domed-wiper seals, etc. to fluidly seal sample holder gear (188) and seal (180). In the present example, sample holder gear (188) is configured to engage a portion of rotatable manifold (310), such as a T-shaped axle, to rotate rotatable manifold (310) when sample holder gear (188) is rotated. As noted above, sample holder motor (280), shown in FIG. 5-6, is operable to engage and rotate rotatable manifold (310) via the meshing of sample holder cog (214) and sample holder gear (188) when probe (102) is coupled to holster (202). Still other constructions for tissue sample holder seal (180) and/or sample holder gear (188) will be apparent to one of ordinary skill in the art in view of the teachings herein.

IV. Exemplary Operation Modes

As discussed above, user interface (526) on control module (500) allows a user to adjust several operational modes to selectively control operation of biopsy device (100). Exemplary operation modes and interfaces will be described below in further detail, while others will be apparent to those of ordinary skill in the art in view of the teachings herein. Additional exemplary operational modes and interfaces are disclosed in U.S. Pat. Pub. No. 2009/0131821, entitled "Graphical User Interface For Biopsy System Control Module," published May 21, 2009 and U.S. Pat. Pub. No. 2009/0131820, entitled "Icon-Based User Interface On Biopsy System Control Module," published May 21, 2009, the disclosures of which are incorporated by reference herein.

Figure 11:
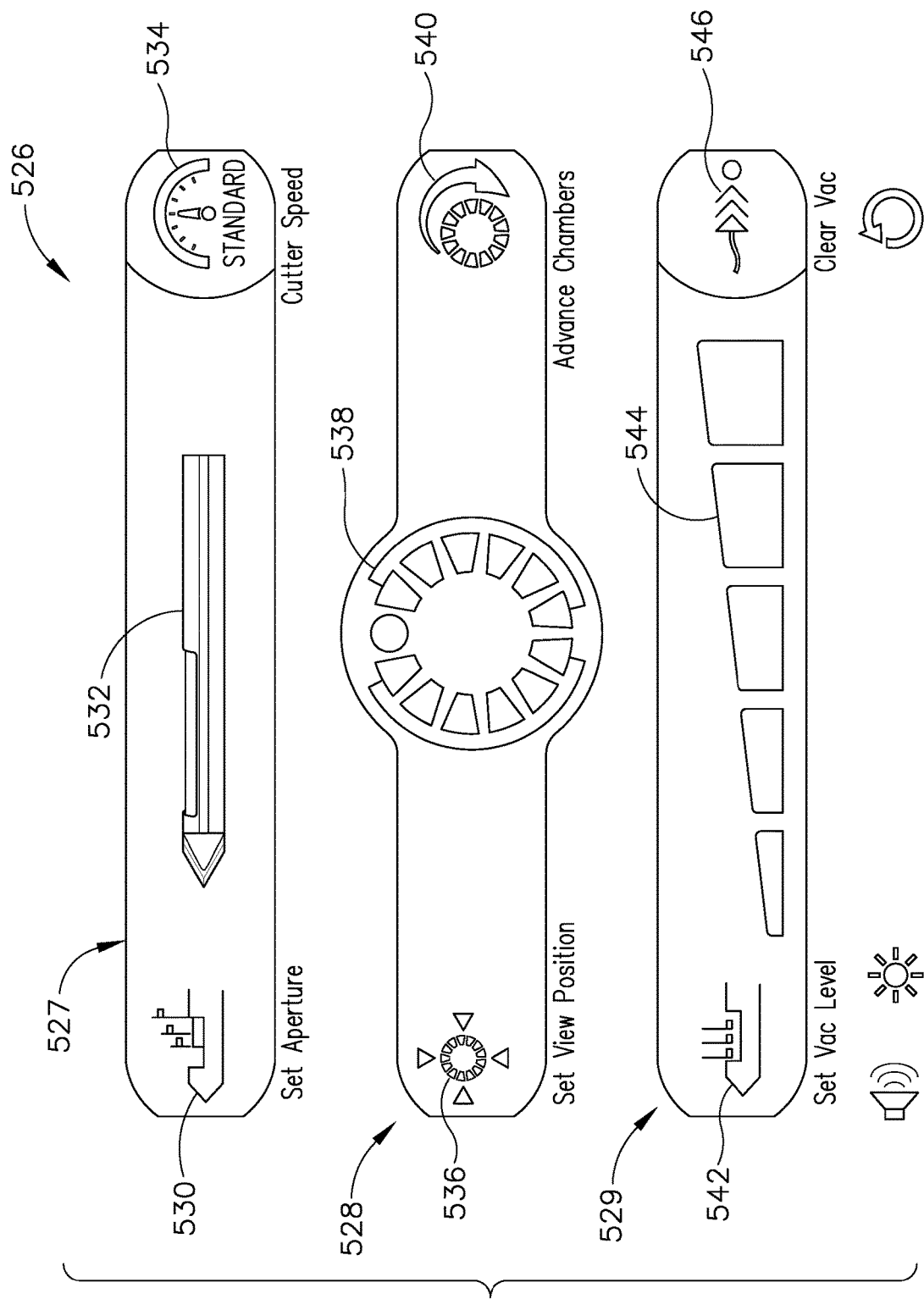
FIG. 11 depicts a front view of an exemplary user interface for the biopsy device of FIG. 2.

FIG. 11 depicts user interface (526) comprising selection bars (527, 528, 529). Each selection bar (527, 528, 529) comprises an operation mode that a user may selectively control by using icons (530, 534, 536, 540, 542, 546). A user may touch the screen of user interface (526) on the selected icon to adjust and/or select an operational mode. Other suitable methods of adjusting and/or selecting operational modes, such as providing a button or a switch on user interface (526) or remotely, will be apparent to one with ordinary skill in the art in view of the teachings herein. Indicators (532, 538, 544) on selection bars (527, 528, 529) display the current or selected operation mode of biopsy device (100).

Cutter selection bar (527) allows a user to select various sequences for cutter (120). Cutter (120) is initially in a distal position to close lateral aperture (112). Cutter (120) is then retracted proximally to open at least a portion of aperture (112) to allow to tissue to prolapse into aperture (112). After tissue enters aperture (112), cutter (120) advances to the distal position. As cutter (120) advances distally, cutter (120) severs the tissue prolapsed into aperture (112) and closes aperture (112). Operation of cutter (120) may be varied by a user. Cutter selection bar (527) comprises an aperture icon (530), speed icon (534), and aperture indicator (532). A user may use aperture icon (530) to adjust the size of aperture (112) with cutter (120) in a manner such that aperture (112) will not open further than a preselected size. It may be desirable to not allow cutter (120) to fully retract proximally in order to acquire tissue samples of a relatively shorter length, to acquire tissue samples that are relatively close to the surface of a patient's skin, or for other purposes. A user may adjust this effective needle aperture (112) by activating aperture icon (530). Each time the user activates aperture icon (530), biopsy system (10) will make a corresponding adjustment to the effective needle aperture (112), such as through control module (500). Such adjustments may be incremental, such as to provide an aperture (112) that is 50%, 75%, or 100% open, though other increments may be used. In addition, each time the user activates aperture icon (530), the cutter portion of aperture icon (530) moves relative to the needle portion of aperture icon (530). Arrows are shown above the cutter portion of aperture icon (530) to emphasize the maximum proximal position of cutter (120) selected by the user. A text representation (e.g., "Sm" for small aperture (112), "Lg" for large aperture (112), etc.) may be included to further indicate the effective aperture (112) size selected by the user.

It may also be desirable to vary the speed of cutter (120). A user may use speed icon (534) to adjust the translational speed of cutter (120) in a manner such that cutter may retract proximally and advance distally at a preselected speed. A user may adjust cutter (120) speed by activating speed icon (534). Each time the user activates speed icon (534), biopsy system (10) will make a corresponding adjustment to cutter (120) speed, such as through control module (500) (e.g. higher or lower). Such adjustments may be incremental. Each time a user activates speed icon (534), the arrow in speed icon (534) may move relative to the hash marks to indicate the relative cutter (120) speed. Cutter (120) may also dwell at the proximal position to allow a sufficient amount of tissue to prolapse into aperture (112). The amount of time cutter (120) dwells at the proximal position may be adjusted based on the selected cutter (120) speed. As cutter (120) speed is increased, cutter (120) dwell time may be reduced. As cutter (120) speed is decreased, cutter (120) dwell time may be increased. Cutter (120) dwell time may be adjusted simultaneously with cutter (120) speed when a user activates speed icon (534) or cutter (120) dwell time may be adjusted separately from cutter (120) speed using a different icon, button, switch, etc. as will be apparent to one with ordinary skill in the art based on the teachings herein.

Aperture indicator (532) may also be provided on user interface (526) screen. As shown in FIG. 11, aperture indicator (532) includes a display of a needle (110) end with a brightly lit cutter (120). Aperture indicator (532) may indicate the current position of cutter (120) within needle (110). As shown in FIG. 11, aperture indicator (532) shows cutter (120) in a fully distal position to close aperture (112). As cutter (120) is retracted proximally, aperture indicator (532) may display cutter (120) retracting proximally on user interface (526). This allows a user to view the actual cutter (120) position and cutter (120) speed to ensure that the selected settings adjusted by aperture icon (530) and speed icon (534) have been properly applied.

Manifold selection bar (528) allows a user to select various sequences for tissue sample holder (302). Manifold (310) of tissue sample holder (302) may be configured to rotate after a tissue sample is acquired, to present the tissue sample to the user for viewing before the user acquires the next tissue sample. As merely an illustrative example, a tissue sample may be drawn into a chamber in manifold (310) that is in the twelve o'clock position when the tissue sample is initially acquired. Manifold (310) is then rotated until the tissue sample is at the three o'clock position, thereby permitting a user to easily view the tissue sample from the side of biopsy device (100). Such rotation may occur substantially immediately after tissue sample is drawn to manifold (310), or biopsy system (10) may wait to see if any user inputs occur within a certain time period (e.g., 2 seconds) after the tissue sample has been acquired, then rotate the tissue sample to the three o'clock position only if no user inputs have occurred within that time period. The rotational position of manifold (310) may be maintained such that tissue sample is kept at the three o'clock position until some other user input is provided. A user may provide input indicating a desire to obtain another tissue sample, biopsy system (10) may rotate manifold (310) to align the next available chamber (e.g., a chamber that is immediately adjacent to the chamber in which the most recently acquired tissue sample resides). As an alternative to waiting for user input, tissue sample may be kept in the three o'clock position for a certain time (e.g., 5 seconds), with manifold (310) being automatically rotated to align the next available chamber with cutter (120), regardless of whether a user has provided an input.

Manifold selection bar (528) comprises a manifold icon (536), an advance icon (540), and a manifold indicator (538). A user may use manifold icon (536) to adjust the rotation of manifold (310) to view the acquired tissue sample such that manifold (310) rotates to a predetermined position. It may be desirable to rotate manifold (310) to various positions to view the tissue sample depending on the user orientation of biopsy device (100) or where the user is positioned relative to biopsy device (100). A user may adjust the rotation of manifold (310) to view the sample by activating manifold icon (536). Each time the user activates manifold icon (536), biopsy system (10) will make a corresponding adjustment to the rotation of manifold (310), such as through control module (500). Such adjustments may be incremental, such as to provide a rotation that is at 90 degree increments, though other increments may be used. In addition, each time the user activates manifold icon (536), an arrow in manifold icon (536) may light up to indicate the corresponding 90 degree increment that the user has selected to position manifold (310) in the tissue viewing position.

It may also be desirable to select a predetermined chamber in manifold (310) in which to transport the acquired tissue sample. A user may use advance icon (540) to rotate manifold (310) incrementally to the immediately adjacent chamber. Each time the user activates advance icon (540), biopsy system (10) will make a corresponding adjustment to the rotation of manifold (310), such as through control module (500). Such adjustments may be incremental to correspond to each chamber in manifold (310), though other increments may be used. Manifold (310) may advance more than one chamber at time, such as in 90 degree or 180 degree increments. Advance icon (540) comprises a display of the chambers in manifold (310) with a dot to illustrate the initial chamber selected to receive a tissue sample. Each time the user activates advance icon (540), the dot may rotate either clockwise or counterclockwise to indicate the corresponding chamber of manifold (310) that the user has selected to receive a tissue sample.

As shown in FIG. 11, manifold selection bar (528) comprises manifold indicator (538). Manifold indicator (538) comprises a display of the chambers of manifold (310). A shaded region covers the currently selected chamber of manifold (310) to receive a tissue sample. As manifold (310) is rotated, other chambers will rotate on manifold indicator (538) under the shaded region. Each chamber of manifold (310) may be numbered on manifold (310) to easily identify a specific chamber. Accordingly, a text representation of the number of the selected chamber of manifold (310) to receive the tissue sample may be indicated on manifold indicator (538) in the center of manifold indicator (538).

Vacuum selection bar (529) comprises level icon (542), clear icon (546), and level indicator (544). Once needle (110) is inserted into a patient with cutter (120) in the distal position, vacuum may be applied to lateral lumen (134) and/or longitudinal lumen (132). With the vacuum applied as described above, cutter (120) is retracted proximally to open aperture (112), which results in tissue prolapsing into aperture (112) under the influence of the above-described vacuum. Cutter (120) may dwell in a retracted position for a certain period of time to ensure sufficient prolapse of tissue. Cutter (120) may then advance distally such that cutter (120) closes aperture (112), the prolapsed tissue is severed and at least initially contained within cutter lumen (136). With vacuum applied and communicated through cutter lumen (136), severed tissue sample may be drawn proximally through cutter lumen (136) and into the selected chamber of manifold (310).

It may be desirable to adjust the vacuum level applied to biopsy device (100) depending on the characteristics (hardness, thickness, etc.) of the tissue to be sampled. A user may adjust the vacuum level by activating level icon (542). Each time the user activates level icon (542), biopsy system (10) will make a corresponding adjustment to the amount of vacuum applied to biopsy device (100), such as through control module (500). Such adjustments may be incremental, such as to provide a selected amount of increase or decrease to the amount of vacuum, though other increments may be used. Level icon (542) may include a set of ascending bars, to indicate the vacuum level of biopsy system (10). To adjust the vacuum level of biopsy system (10), the user may activate level icon (542). Each time the user activates level icon (542), the vacuum level of biopsy system (10) may increase incrementally. Such incremental increase may be indicated by illuminating an additional bar in the set of ascending bars of level icon (542). The number of bars that are illuminated in level icon (542) may be indicative of the vacuum level of biopsy system (10). If the user activates level icon (542) when all of the bars are illuminated (e.g., which may indicate that the vacuum level is at its highest), the level of vacuum may be significantly decreased to the lowest level, such that only the first bar in the set of bars is illuminated. Thus, a user may cycle through various incremental vacuum levels by repeatedly activating level icon (542).

At some point during use of biopsy device (100), biopsy device (100) may exhibit signs of being jammed with tissue or other debris. Such signs will be apparent to one with ordinary skill in the art in view of the teachings herein. During such times, or otherwise, it may be desirable to initiate a sequence that may clear such tissue or debris in order to improve performance of biopsy device (100). Clear icon (546) may be activated to initiate such sequence. When a user activates the clear icon (546) a maximum amount of vacuum may be applied to biopsy device (100) for a certain period of time. Other suitable clearing methods (e.g., translating cutter back and forth, flushing saline, etc.) will be apparent to one with ordinary skill in the art based on the teachings herein.

As shown in FIG. 11, vacuum selection bar (529) comprises level indicator (544). Level indicator (544) comprises a set of bars in ascending heights to indicate the actual vacuum level applied to biopsy device (100). As vacuum is applied to biopsy device (100), a corresponding bar may be illuminated to indicate the level of vacuum applied to biopsy device (100). Each ascending bar indicates a level of vacuum such that illumination of a higher bar corresponds to a higher level of vacuum, while illumination of a lower bar corresponds to a lower level of vacuum. Accordingly, as actual vacuum is applied to biopsy device (100), the set of bars on level indicator (544) may illuminate to depict the level of vacuum applied to biopsy device (100) to the user. Other suitable methods of indication will be apparent to one with ordinary skill in the art in view of the teachings herein.

IV. Exemplary Control

Figure 12:
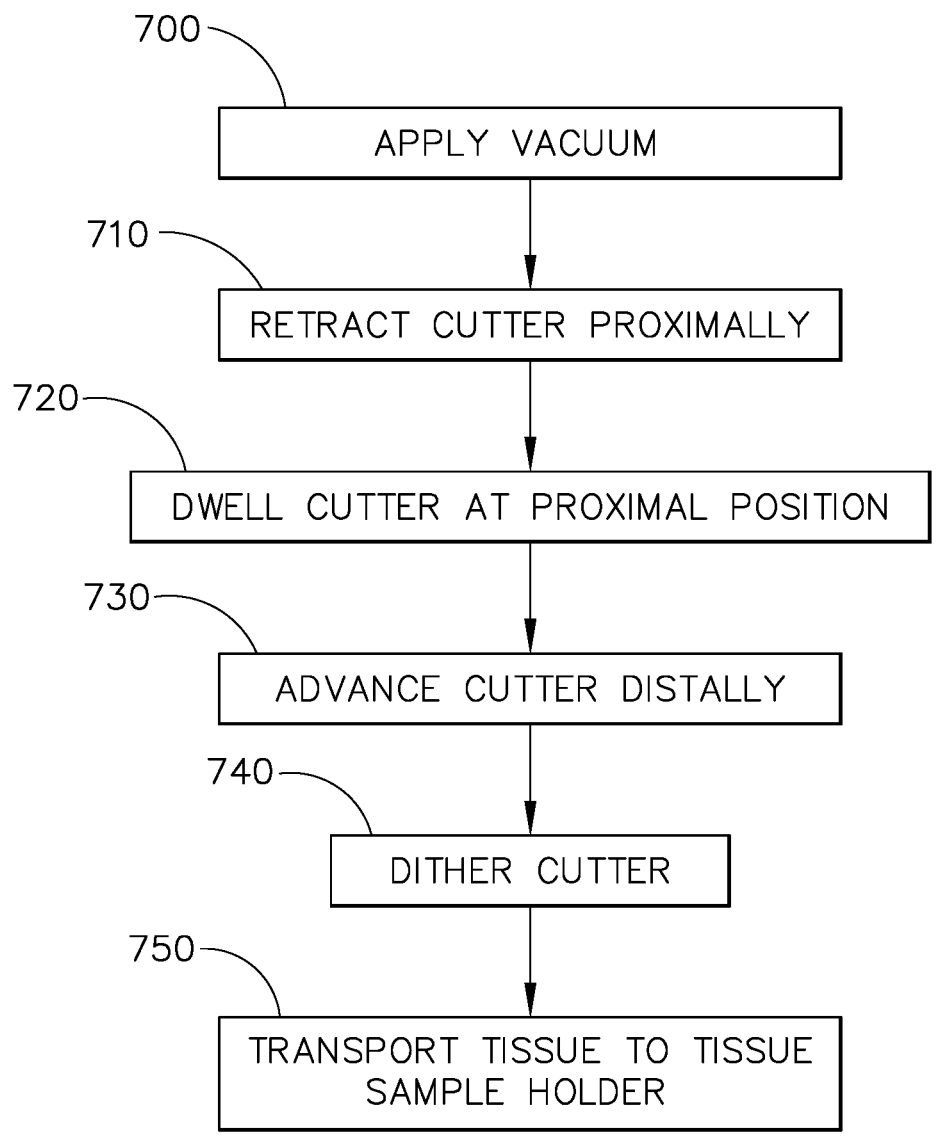
FIG. 12 depicts a flowchart of an exemplary control for the biopsy device of FIG. 2.

An exemplary control to operate biopsy system (10) is shown in FIG. 12. Step (700) comprises applying a vacuum to biopsy device (100). Control module (500) may be activated to fluidly apply vacuum to lateral lumen (134) and/or longitudinal lumen (132) at the vacuum level preselected by level icon (542). In step (710), cutter (120) is retracted to a proximal position to open at least a portion of lateral aperture (112). Cutter (120) is retracted to the preselected proximal position by aperture icon (530) at the preselected speed by speed icon (534). Cutter (120) may be retracted while vacuum is being generated to biopsy device (100) or cutter (120) may be retracted after vacuum has been generated to a desired level to biopsy device (100). Once lateral aperture (112) is open to the predetermined position, tissue may be prolapsed into lateral aperture (112). Cutter (120) may dwell at a proximal position, as shown in step (720), to allow a sufficient amount of tissue to be prolapsed into lateral aperture (112). Step (730) comprises advancing cutter (120) distally to close lateral aperture (112) at the preselected speed by speed icon (534). As cutter (120) advances distally, the prolapsed tissue in lateral aperture (112) is severed by cutter (120) within needle (110). Cutter (120) may optionally dither by oscillating proximally and distally to ensure that tissue is fully severed within needle (110), as shown in step (740). With vacuum applied to biopsy device (100) at the preselected level by level icon (542), the severed tissue may then be transported through cutter lumen (136) from lateral aperture (112) to tissue sample holder (302) in step (750). The tissue sample is deposited into the preselected chamber of manifold (310) by advance icon (540).

Cycle time is measured by the amount of time required to take a tissue sample. The cycle begins when vacuum is activated in step (700) and ends when the tissue sample is deposited in tissue sample holder (302) after step (750). The size of the tissue sample may depend on the amount of cycle time to take a tissue sample. A longer cycle time may allow for a larger tissue sample, while a shorter cycle time may result in a smaller tissue sample. The size of the tissue sample may depend on cycle time due to such factors as the translational and/or rotational speed of cutter (120), the dwell time of cutter (120), the amount of dithers cutter (120) performs, the amount of vacuum pressure applied to biopsy device (100), the amount of time to transport tissue from lateral aperture (112) to tissue sample holder (302), etc. Other suitable factors will be apparent to one with ordinary skill in the art in view of the teachings herein. It may be desirable to optimize the cycle time and/or the tissue sample size by adjusting such cycle time factors as discussed below.

Figure 13:
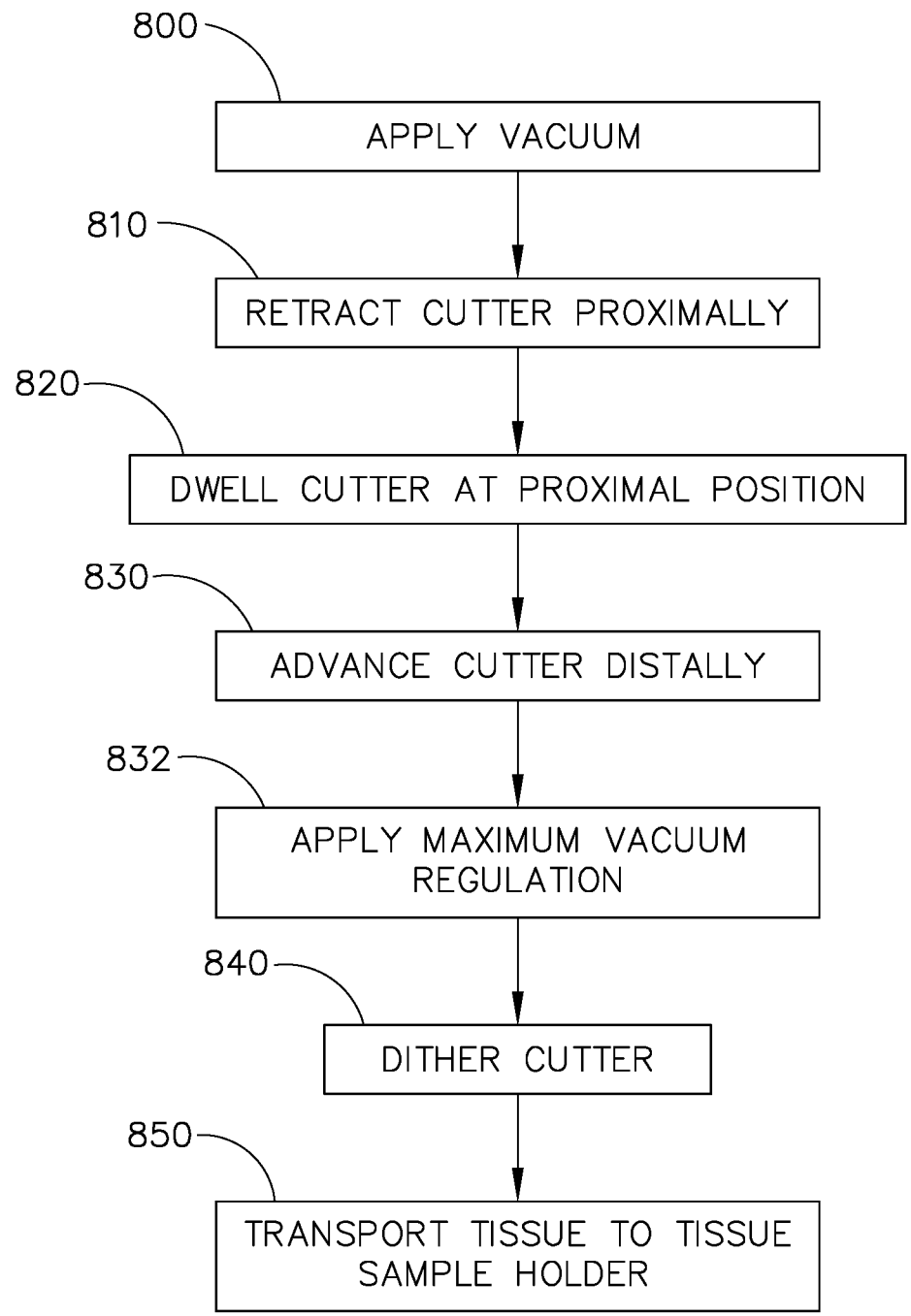
FIG. 13 depicts a flowchart of another exemplary control for the biopsy device of FIG. 2.

FIG. 13 depicts an exemplary control for vacuum regulation to biopsy device (100). The control shown in FIG. 13 is similar to the control shown in FIG. 12, except that the control of FIG. 13 has an additional step (832). Step (832) comprises applying maximum vacuum regulation to biopsy device (100) after advancing cutter (120) distally. As discussed above, a user may vary vacuum regulation to biopsy device (100) by user interface (526) on control module (500) to selectively increase or decrease vacuum pressure. If a user has adjusted the vacuum pressure to biopsy device (100) below the available maximum amount of vacuum pressure, the amount of time required to transport the severed tissue sample from lateral aperture (112) to tissue sample holder (302) may increase because of the lower amount of vacuum pressure applied to biopsy device (100), thus increasing the cycle time. Step (832) overrides the vacuum pressure adjustment made by a user with user interface (526) to apply maximum vacuum pressure to biopsy device (100) after cutter (120) has advanced distally. By waiting to apply maximum vacuum pressure after cutter (120) advances distally, a user may still selectively adjust vacuum pressure to biopsy device (100) by user interface (526) to prolapse tissue at selected levels into lateral aperture (112). Step (832) may also be performed after cutter (120) dithers, as shown in step (840) if a dither step is performed.

The available maximum vacuum pressure may be determined by comparing the ambient pressure with the maximum pressure that may be generated with control module (500). Ambient pressure may be measured with a pressure sensor in control module (500), on biopsy device (100), or at other suitable sensor locations on biopsy system (10) as will be apparent to one with ordinary skill in the art based on the teachings herein. Maximum pressure generated by control module (500) may be determined by fully activating vacuum source (510) until the vacuum levels to a substantially steady pressure. Pressure generated by control module (500) may also be measured by a pressure sensor in control module (500), on biopsy device (100), or at other suitable locations on biopsy system (10) as will be apparent to one with ordinary skill in the art. The pressure may be substantially steady when the pressure substantially remains within a predetermined range for a predetermined amount of time. Once the pressure generated by control module (500) reaches a substantially steady maximum pressure, the difference between the maximum pressure and ambient pressure may be determined for the maximum vacuum pressure available to biopsy device (100). The maximum vacuum pressure may vary depending on ambient pressure, etc. A minimum amount of vacuum pressure may be determined by the minimum amount of vacuum pressure required to transport a tissue sample through cutter lumen (136) to tissue sample holder (302). The control may disable biopsy device (100) from use if the determined maximum vacuum pressure is below the minimum amount of vacuum pressure required to transport tissue to tissue sample holder (302).

Figure 14:
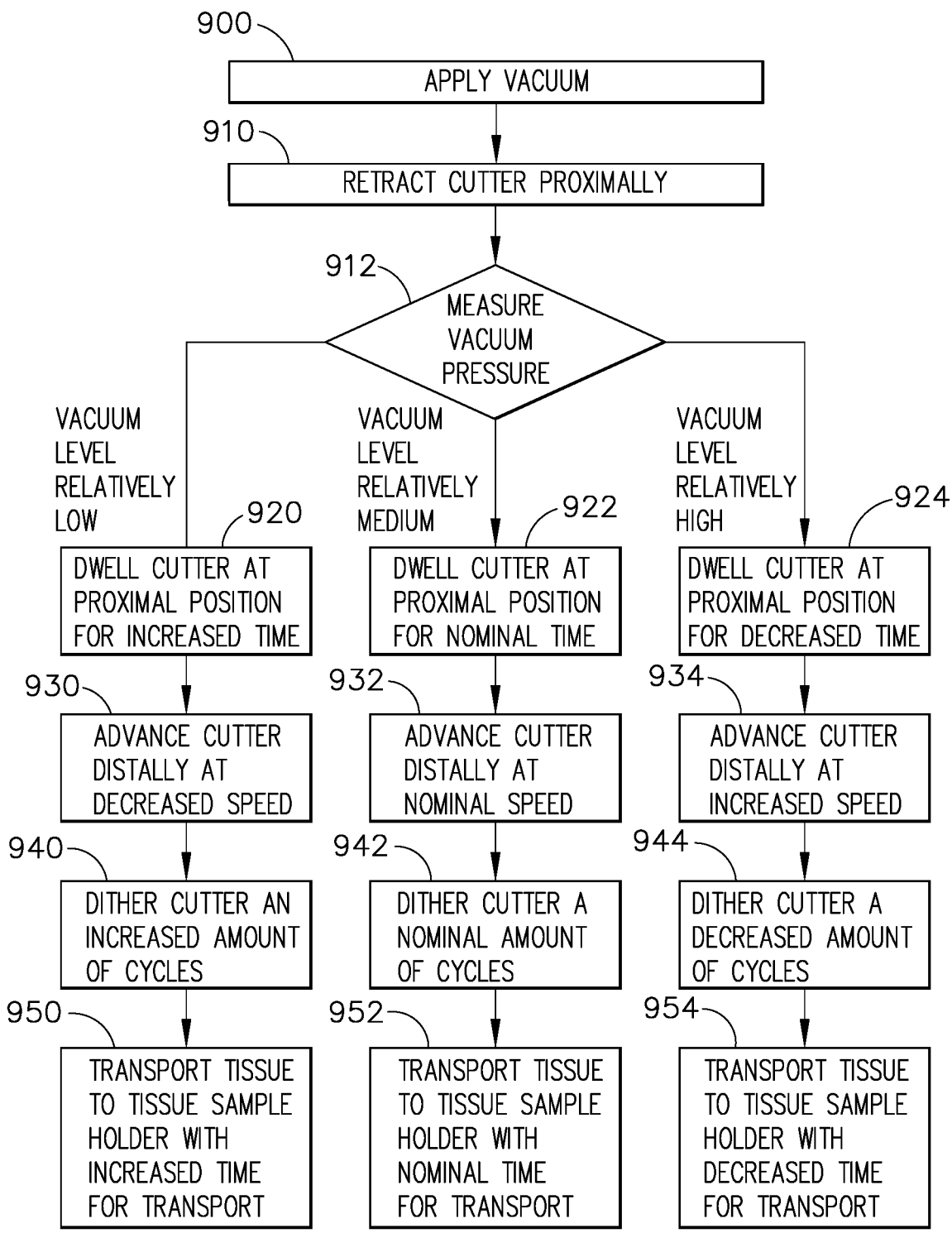
FIG. 14 depicts a flowchart of another exemplary control for the biopsy device of FIG. 2.

Another exemplary control for vacuum regulation to biopsy device (100) is shown in FIG. 14. The control shown in FIG. 14 is similar to the control shown in FIG. 12, except that the control of FIG. 14 measures actual vacuum pressure as depicted in step (912). Actual vacuum pressure may be measured with a pressure sensor in control module (500), on biopsy device (100), or at other suitable sensor locations on biopsy system (10) as will be apparent to one with ordinary skill in the art based on the teachings herein. Various elements of biopsy device (100) (such as cutter (120) rotational and/or translational speed, dwell time of cutter (120), amount of dithers of cutter (120), amount of time to transport tissue to tissue sample holder (302), etc.) may then be adjusted based on the measured vacuum pressure.

Once vacuum pressure is measured in step (912), the level of vacuum pressure may be categorized. As shown in FIG. 14, vacuum pressure may be categorized into three levels such as relatively low, relatively medium, and relatively high. Other suitable number of level categories and type of categories will be apparent to one with ordinary skill in the art based on the teachings herein. Based on the category, biopsy system (10) may be adjusted from the nominal user preselected settings. If the vacuum level is categorized as relatively low, step (920) may be followed to dwell cutter (120) for an increased amount of time above the nominal amount of time. Next, cutter (120) may be advanced distally at a decreased speed below the nominal speed as in step (930). Step (940) comprises dithering cutter (120) an increased amount of cycles above the nominal amount of cycles. At relatively low vacuum pressure, the amount of time to transport tissue from lateral aperture (112) to tissue sample holder (302) may be increased above a nominal transport time as depicted in step (950). Dwelling cutter (120) for an increased amount of time, advancing cutter (120) at a decreased speed, dithering cutter (120) an increased amount of times, and allowing an increased amount of tissue transport time allows tissue to be sufficiently prolapsed into lateral aperture (112) and transported to tissue holder (302) with a sufficient tissue sample size with a relatively low vacuum pressure. It should be noted that any one of steps (920, 930, 940, 950) may be applied individually or in combination to optimize the desired tissue sample size and cycle time at a relatively low vacuum pressure.

After step (912), if vacuum pressure is at a relatively nominal level, the nominal or preselected settings may be used. Cutter (120) may dwell at a proximal position for a nominal amount of time as shown in step (922). Cutter (120) may then advance distally at a nominal speed, step (932), and dither for a nominal amount of cycles, step (942). Tissue may be transported to tissue sample holder (302) in a nominal amount of time. It should be noted that any one of steps (922, 932, 942, 952) may be applied individually or in combination to optimize the desired tissue sample size and cycle time at a relatively medium vacuum pressure.

If vacuum pressure is categorized as relatively high, step (924) may be applied, which comprises dwelling cutter (120) at a proximal position for a decreased amount of time, or a decreased amount of time below the nominal cutter (120) dwell time. Step (934) comprises advancing cutter (120) distally at an increased speed above the nominal advancement speed. The amount of cutter (120) dither cycles may be decreased below nominal, as shown in step (944). The amount of cutter (120) dither cycles may also be bypassed as will be apparent to one with ordinary skill in the art based on the teachings herein. Tissue may be transported from lateral aperture (112) to tissue sample holder (302) in a decreased amount of time below nominal, as in step (954). Dwelling cutter (120) for a decreased amount of time, advancing cutter (120) at an increased speed, decreasing cutter (120) dither cycles, and decreasing the amount of tissue transport time allows tissue to be sufficiently prolapsed into lateral aperture (112) and transported to tissue sample holder (302) with a sufficient tissue sample size at a relatively high vacuum pressure and a lower cycle time. It should be noted that any one of steps (924, 934, 944, 954) may be applied individually or in combination to optimize the desired tissue sample size and cycle time at a relatively high vacuum pressure.

Vacuum pressure may be measured after step (910), or selectively after each step shown in FIG. 14. If vacuum pressure levels vary between steps, vacuum pressure may be recategorized after any step in FIG. 14 to adjust control of biopsy device (100) after each step or a selected number of steps. As an illustrative example, if vacuum pressure is measured in step (912) and categorized as relatively high, step (924) may be applied to dwell cutter (120) for an increased amount of time. If vacuum pressure is measured again after step (924), it may be recategorized as relatively medium and step (932) may be applied to advance cutter (120) at a nominal speed. Vacuum pressure may be measured and/or recategorized after any selected step. Other suitable variations will be apparent to one with ordinary skill in the art in view of the teachings herein.

Figure 15:
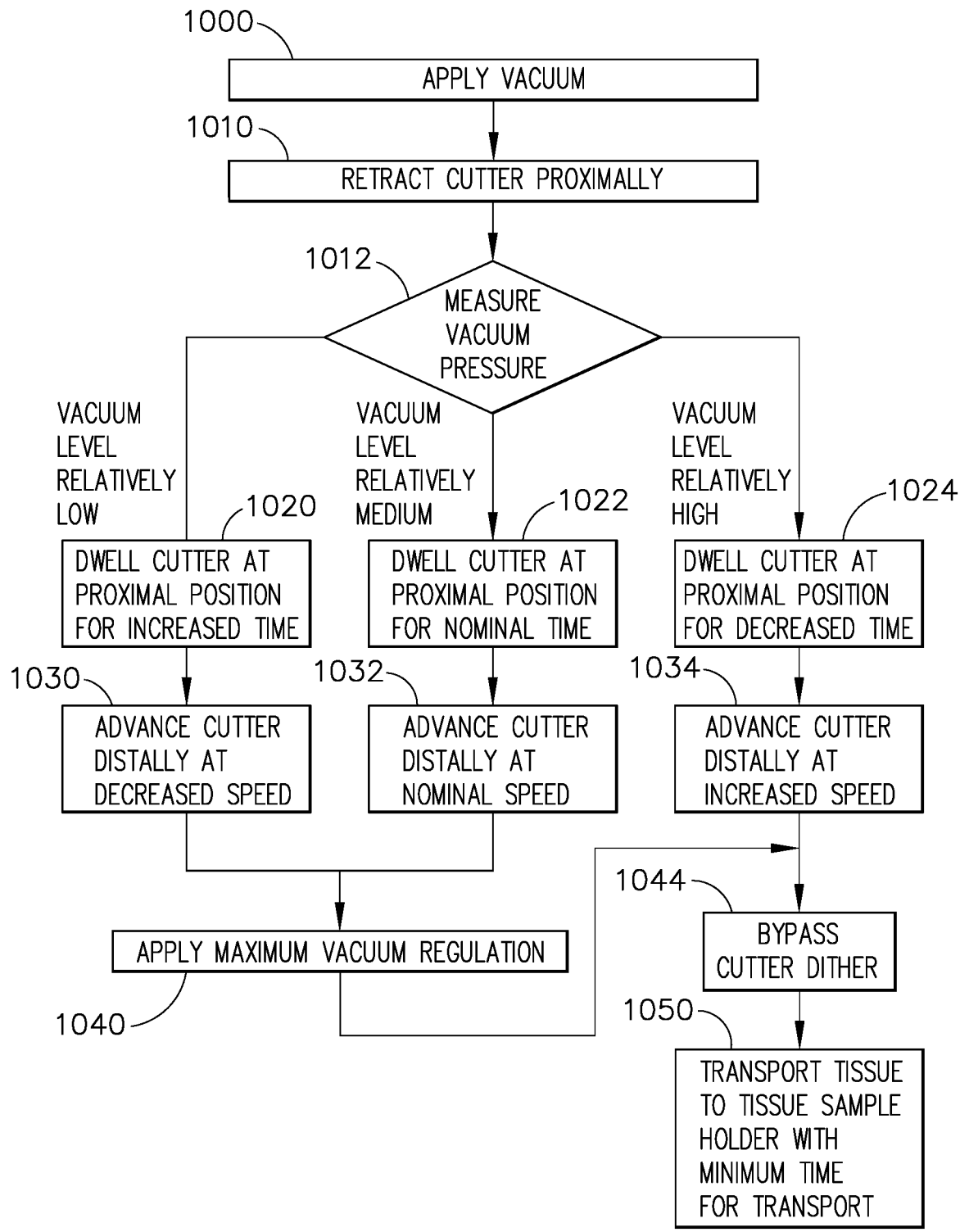
FIG. 15 depicts a flowchart of another exemplary control for the biopsy device of FIG. 2.

Another exemplary control for biopsy device (100) is depicted in FIG. 15. The exemplary control shown in FIG. 15 is similar to the exemplary control of FIG. 14, except that maximum vacuum regulation is applied after closing lateral aperture (112). Similarly to the control of FIG. 14, the control of FIG. 15 measures vacuum pressure in step (1012) and categorizes the level of vacuum pressure into three categories, such as relatively low, relatively medium, and relatively high. Other suitable number of level categories and type of categories will be apparent to one with ordinary skill in the art based on the teachings herein. As described above, if vacuum pressure is relatively low, cutter (120) may dwell at a proximal position for an increased amount of time (step 1020) and/or cutter (120) may be advanced distally at a decreased speed (step 1030). If vacuum pressure is relatively medium, cutter (120) may dwell for a nominal amount of time (step 1022) and/or cutter (120) may be advanced proximally at a nominal speed (step 1032). If vacuum pressure is relatively high, cutter (120) may dwell at a proximal position for a decreased amount of time (step 1024) and/or cutter (120) may be advanced distally at an increased speed (step 1034). Any one of steps (1020, 1022, 1024, 1030, 1032, 1034) may be applied individually or in combination to optimize the desired tissue sample size and cycle time.

Vacuum pressure may be measured after step (1010), or selectively after each step shown in FIG. 15. If vacuum pressure levels vary between steps, vacuum pressure may be recategorized after any step in FIG. 14 to adjust control of biopsy device (100) after each step or a selected number of steps. As an illustrative example, if vacuum pressure is measured in step (1012) and categorized as relatively high, step (1024) may be applied to dwell cutter (120) for an increased amount of time. If vacuum pressure is measured again after step (1024), it may be recategorized as relatively medium and step (1032) may be applied to advance cutter (120) at a nominal speed. Vacuum pressure may be measured and/or recategorized after any selected step. Other suitable variations will be apparent to one with ordinary skill in the art in view of the teachings herein.

Once cutter (120) is advanced to a distal position to close lateral aperture (112) and sever tissue, maximum vacuum regulation may be applied to biopsy device (100) (step (1040). As discussed above, a user may vary vacuum regulation to biopsy device (100) by adjusting user interface (526) on control module (500) to selectively increase or decrease vacuum pressure. If a user has adjusted the vacuum pressure to biopsy device (100) below the available maximum amount of vacuum pressure, the amount of time required to transport the severed tissue sample from lateral aperture (112) to tissue sample holder (302) may increase because of the lower amount of vacuum pressure applied to biopsy device (100), thus increasing the cycle time. Step (1040) overrides the vacuum pressure adjustment made by a user with user interface (526) to apply maximum vacuum pressure to biopsy device (100) after cutter (120) has advanced distally. With maximum vacuum pressure applied to biopsy device (100), cutter (120) dither may be decreased or bypassed (step 1044) and/or a minimum amount of time to transport tissue from lateral aperture (112) to tissue sample holder (302) may be applied (step 1050). Steps (1044) and (1050) may decrease cycle time while still allowing a desired tissue sample size. By waiting to apply maximum vacuum pressure after cutter (120) advances distally, a user may still selectively adjust vacuum pressure to biopsy device (100) by user interface (526) to prolapse tissue at selected levels into lateral aperture (112). Any one of steps (1044, 1050) may be applied individually or in combination to optimize the desired tissue sample size and cycle time.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Embodiments of the devices disclosed herein can be reconditioned for reuse after at least one use. Reconditioning may include any combination of the steps of disassembly of the device, followed by cleaning or replacement of particular pieces, and subsequent reassembly. In particular, embodiments of the devices disclosed herein may be disassembled, and any number of the particular pieces or parts of the devices may be selectively replaced or removed in any combination. Upon cleaning and/or replacement of particular parts, embodiments of the devices may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A biopsy system comprising a biopsy device, wherein the biopsy device comprises a probe, wherein the biopsy system comprises:
    (a) a needle, wherein the needle extends distally from the probe,
    (b) a cutter, wherein the cutter is movable relative to the needle,
    (c) a tissue sample holder, wherein the tissue sample holder is detachably coupled to a proximal end of the probe;
    (d) a vacuum source, wherein the vacuum source is configured to apply vacuum to the cutter at predetermined vacuum levels between a maximum vacuum level and a minimum vacuum level; and
    (e) a processing module including an interface configured to permit an operator to selectively increase or decrease the vacuum provided to the cutter to a user selected vacuum level;
    wherein the processing module is operable in a cycle to provide the vacuum to the cutter at the user selected vacuum level using the vacuum source, retract the cutter to a proximal position, advance the cutter to a distal position, and oscillate the cutter between the distal position and an intermediate position, wherein the intermediate position is disposed proximally of the distal position; and
    wherein the processing module is further configured to apply an override vacuum level corresponding to the maximum vacuum level to the cutter using the vacuum source when the cutter is in the distal position, wherein the biopsy system is operable to override the user selected vacuum level when the vacuum provided to the cutter is adjusted to the override vacuum level.

2. The biopsy system of claim 1, wherein the processing module is further configured to apply the override vacuum level to the cutter when the cutter is oscillating between the distal position and the intermediate position.

3. The biopsy system of claim 1, wherein the processing module is operable to increase the vacuum provided to the cutter after the cutter translates from the proximal position to the distal position.

4. The biopsy system of claim 3, wherein biopsy processing module is operable to adjust the vacuum provided to the cutter to the override vacuum level after the cutter translates from the proximal position to the distal position.

5. A method for operating a biopsy system, wherein the biopsy system comprises a biopsy device, wherein the biopsy device comprises a probe, a needle distally extending from the probe, a cutter movable relative to the needle, and a tissue sample holder detachably coupled to a proximal end of the probe, the method comprising:
    (a) applying a selected amount of vacuum to the biopsy device at a user selected level;
    (b) retracting the cutter to a proximal position;
    (c) dwelling the cutter at the proximal position;
    (d) advancing the cutter to a distal position;
    (e) applying an override vacuum corresponding to a maximum available vacuum level to the biopsy device automatically after advancing the cutter to override the selected amount of vacuum; and (f) oscillating the cutter between the distal position and an intermediate position, wherein the intermediate position is between the distal position and the proximal position.

\* \* \* \* \*